US012322514B1

(12) United States Patent
Tang

(10) Patent No.: US 12,322,514 B1
(45) Date of Patent: Jun. 3, 2025

(54) SYSTEM FOR ONLINE PREVENTATIVE HEALTHCARE COUNSELING AND HEALTH INTERVENTION PROGRAM SERVICES

(71) Applicant: Yaqing Tang, Newton Highlands, MA (US)

(72) Inventor: Yaqing Tang, Newton Highlands, MA (US)

( * ) Notice: Subject to any disclaimer, the term of this patent is extended or adjusted under 35 U.S.C. 154(b) by 273 days.

(21) Appl. No.: 17/967,202

(22) Filed: Oct. 17, 2022

Related U.S. Application Data

(60) Provisional application No. 63/256,591, filed on Oct. 17, 2021.

(51) Int. Cl.
| | |
|---|---|
| *G16H 50/30* | (2018.01) |
| *G06Q 30/0226* | (2023.01) |
| *G16H 10/20* | (2018.01) |
| *G16H 10/60* | (2018.01) |
| *G16H 20/30* | (2018.01) |

(Continued)

(52) U.S. Cl.
CPC ......... *G16H 50/30* (2018.01); *G06Q 30/0231* (2013.01); *G06Q 30/0233* (2013.01); *G16H 10/20* (2018.01); *G16H 10/60* (2018.01); *G16H 20/30* (2018.01); *G16H 20/60* (2018.01); *G16H 20/70* (2018.01)

(58) Field of Classification Search
None
See application file for complete search history.

(56) References Cited

U.S. PATENT DOCUMENTS

| | | | |
|---|---|---|---|
| 9,734,295 B1 * | 8/2017 | Movva | ............... A61B 5/747 |
| 9,798,860 B1 | 10/2017 | Movva | |

(Continued)

FOREIGN PATENT DOCUMENTS

| | | |
|---|---|---|
| CN | 102650994 A | 8/2012 |
| WO | 2004010254 A3 | 1/2004 |

(Continued)

OTHER PUBLICATIONS

Basu et al., Regression Estimators for Generic Health-Related Quality of Life and Quality-Adjusted Life Years, Medical Decision Making/Jan.-Feb. 2012.*

*Primary Examiner* — David J Stoltenberg
(74) *Attorney, Agent, or Firm* — Bold IP PLLC; Houda El-Jarrah

(57) ABSTRACT

A computer implemented preventative health care and health intervention application is described. The application includes a scoring system to score an overall health of the member, including breakdowns scoring the member's initial physical health, mental health, and an initial score for the lifestyle of the member. One or more health care providers are assigned to and/or selected by the user. The health care providers assess which health intervention programs are best suited to meet the goals of the member and to improve the score for the member's health. The score is re-evaluated when the member meets a minimum threshold of participation and attendance in the one or more selected health and health intervention programs. The score evaluation includes review of attendance, participation information, data collected from sensors and wearable devices, as well as based on predictive analytics integrated into the preventative health care and health intervention program.

10 Claims, 14 Drawing Sheets

(51) Int. Cl.
*G16H 20/60* (2018.01)
*G16H 20/70* (2018.01)

(56) References Cited

U.S. PATENT DOCUMENTS

| | | | |
|---|---|---|---|
| 10,165,113 B1 | 12/2018 | Nusbaum | |
| 11,429,885 B1* | 8/2022 | McNair | G16H 10/60 |
| 11,456,080 B1* | 9/2022 | Jain | A61B 5/4815 |
| 2005/0234742 A1* | 10/2005 | Hodgdon | G06Q 10/10 |
| | | | 705/2 |
| 2005/0246185 A1 | 11/2005 | Brown | |
| 2013/0226608 A1* | 8/2013 | Di Lascia | G16H 20/70 |
| | | | 705/2 |
| 2015/0012301 A1 | 1/2015 | Weschler et al. | |
| 2015/0112716 A1 | 4/2015 | Hunkeler et al. | |
| 2016/0180050 A1 | 6/2016 | Holmes et al. | |
| 2017/0199189 A1 | 7/2017 | Wade | |
| 2017/0242962 A1 | 8/2017 | Lenchitsky | |
| 2017/0300648 A1 | 10/2017 | Charlap | |
| 2017/0372026 A1 | 12/2017 | Sanyal et al. | |
| 2018/0268922 A1 | 9/2018 | Greene | |
| 2018/0340927 A1 | 11/2018 | Dahl | |
| 2019/0148025 A1 | 5/2019 | Stone et al. | |
| 2019/0156955 A1* | 5/2019 | Winlo | G16H 15/00 |
| 2019/0180879 A1* | 6/2019 | Jain | G16H 10/20 |
| 2019/0290172 A1 | 9/2019 | Hadad et al. | |
| 2019/0355271 A1 | 11/2019 | Dawson | |
| 2020/0005908 A1* | 1/2020 | Yacobi | G16H 40/20 |
| 2020/0082927 A1 | 3/2020 | Hernandez | |
| 2020/0185100 A1 | 6/2020 | Francois | |
| 2021/0015415 A1* | 1/2021 | Ofir | A61B 5/1118 |
| 2021/0027870 A1 | 1/2021 | West | |
| 2021/0065854 A1* | 3/2021 | Hanold | G16H 15/00 |
| 2021/0319887 A1* | 10/2021 | Derrick, Jr. | A61B 5/7275 |
| 2021/0338170 A1* | 11/2021 | Ochiai | A61B 5/374 |
| 2021/0375437 A1* | 12/2021 | Vasudevan | A61B 5/7435 |
| 2021/0375472 A1* | 12/2021 | Czerniecki | G16H 10/60 |
| 2022/0358389 A1* | 11/2022 | McNair | G06N 7/01 |
| 2022/0375616 A1* | 11/2022 | Yu | G06F 16/285 |

FOREIGN PATENT DOCUMENTS

| | | |
|---|---|---|
| WO | 2010009278 A2 | 1/2010 |
| WO | 2021061061 A1 | 4/2021 |

* cited by examiner

Physical Health (The following table shows the body systems categorized by the ICD-10-i codes by WHO) — 260

| System | Health Points |
| --- | --- |
| Central Nervous System | 1 |
| Peripheral Nervous System | 1 |
| Heart And Great Vessels | 1 |
| Upper Arteries | 1 |
| Lower Arteries | 1 |
| Upper Veins | 1 |
| Lower Veins | 1 |
| Lymphatic And Hemic System | 1 |
| Eye | 1 |
| Ear, Nose, Sinus | 1 |
| Respiratory System | 1 |
| Mouth And Throat | 1 |
| Gastrointestinal System | 1 |
| Hepatobiliary System And Pancreas | 1 |
| Endocrine System | 1 |
| Skin And Breast | 1 |
| Subcutaneous Tissue And Fascia | 1 |
| Muscles | 1 |
| Tendons | 1 |
| Bursae And Ligaments | 1 |
| Head And Facial Bones | 1 |
| Upper Bones | 1 |
| Lower Bones | 1 |
| Upper Joints | 1 |
| Lower Joints | 1 |
| Urinary System | 1 |
| Female Reproductive System | 1 |
| Male Reproductive System | 1 |
| Anatomic Region, General | 1 |
| Anatomical Region, Upper Extremities | 1 |
| Anatomic Region, Lower Extremities | 1 |

FIG. 2B

Mental Health (Psychological Well-Being) — 266

| System | Health Points |
|---|---|
| Life Purpose | 1 |
| Mastery | 1 |
| Positive Affect | 1 |
| Optimism | 1 |
| Personal Growth | 1 |
| Autonomy | 1 |
| Sense Of Coherence | 1 |
| Emotional Vitality | 1 |
| Stress Reduction | 1 |
| Intellectual Capabilities | 1 |
| Spiritual Wellness | 1 |
| Life Satisfaction | 1 |
| Cognitive Capabilities | 1 |

FIG. 2C

Social Wellbeing — 268

| System | Health Points |
|---|---|
| Connectedness with Family | 1 |
| Connectedness with Friends | 1 |
| Connectedness with Community | 1 |
| Connectedness with Culture | 1 |
| Self-Acceptance | 1 |
| Helping Others | 1 |
| Engagement of Group Activities | 1 |
| Engagement in Meaningful Conversations | 1 |
| Acquirement of Life Values | 1 |

FIG. 2D

SYSTEM FOR ONLINE PREVENTATIVE HEALTHCARE COUNSELING AND HEALTH INTERVENTION PROGRAM SERVICES

CROSS-REFERENCE TO RELATED APPLICATIONS

This application is a non-provisional application which claims priority to U.S. Provisional Patent Application No. 63/256,591 filed on Oct. 17, 2021, which is incorporated by reference in its entirety.

FIELD OF THE DISCLOSURE

This disclosure relates generally to a system and method for a computer implemented preventative health care and lifestyle counseling and monitoring health intervention program services, which are intervention programs that include but not limited to standard physical, mental or social health intervention programs modifying patients' lifestyles and habits and/or provide patients with preventive care medical or nonmedical services with the support of preventive care technologies to prevent diseases and to stay healthy.

BACKGROUND

Contemporary medical studies have successfully identified many healthy habits such as balanced diet, exercise, high-quality sleep, and social connectedness that can prevent chronic diseases. However, many people still become ill due to a lack of adopting effective lifestyle changes or maintaining healthy habits as they age. Annual checkups are the only preventive services available to patients, but yearly 40-minute sessions with brief counseling are not sufficient for health providers (physicians, nurse practitioners, physician assistants and other qualified health professionals) to persuade patients to make effective lifestyle changes. During an annual checkup, providers spend limited time educating patients about behaviors that can impact health outcomes and rarely address questions related to food consumption, exercise, work conditions, social connections, not to mention other modern lifestyle risks, such as overuse and misuse of electronic devices, sleep deprivation, and stress at work. Additionally, although some providers address the importance of healthy lifestyles to patients, providers' exhortations alone cannot help patients make effective changes. Lastly, the current health system cannot support the effective implementation of preventive health counseling services. For instance, the United States Preventive Services Taskforce (USPSTF) recommends diet and exercise counseling sessions for patients with cardiovascular diseases risks and require multiple intervention sessions throughout a long period of time to be effective; however, providers have limited capacity to deliver such interventions and rarely refer patients to other diet or exercise professionals, nor could they acquire knowledge about whether the patients have complied to their recommendations or not.

Additionally, while there are a variety of personal trainers, fitness classes, and athletic programs available that people may join, these programs are not administered or adopted in conjunction with medical professionals or oversight. It may be easy for a person to focus on losing weight when enrolled in a personal training program, but not focus on other health related aspects that a medical professional can spot and focus on in order to have a full program for preventative care.

Further, there is not an existing program that combines all the above counseling for medical care with a focus on preventive care, with education and coaching regarding nutrition, mental health, lifestyle, quality of sleep, financial wellbeing, healthy housing, and healthy entertainment recommendations that may be made to improve one's overall health. Further, there is a lack of incentive to commit to and excel in such programs without existing incentives within such a program. Accordingly, the one or more systems and methods as described below may overcome the one or more deficiencies noted above.

SUMMARY

A computer implemented method for a preventative care and health intervention application is presented. In a non-limiting embodiment, the computer-implemented method comprises evaluating eligibility of an applicant for one or more preventative health care and health intervention programs. Responsive to the applicant being eligible, enrolling the applicant and converting the applicant to a member further comprising activating a profile of the member in the preventative care and health intervention application and gathering a member's demographic and geographic data and medical history by obtaining current and historical medical data associated with the member, wherein the medical history covers both physical and mental medical history as well as includes information about social health and existing lifestyle of the member, as well as assigning one or more health providers to the member to communicate with the member through the preventative care and health intervention application. The computer implemented method may further include evaluating the member's overall health risks based on several factors comprising member medical history, family history, occupation, lifestyle, nutrition, daily activities, and health risks that relate to a physical health, a mental health, and a social health of the member and providing an initial score of an overall health score of the member that includes physical health, mental health, and social health of the member, and recommending select programs from one or more health intervention programs to the member that assist the member improve their initial score. The computer implemented method may further include setting participation and performance goals of the recommended health intervention programs for the member and assigning health scores to the recommended lifestyle intervention select programs wherein the member can acquire these health scores by achieving the participation and performance goals and tracking progress of the member in following the select programs from the one or more preventative healthcare programs and health intervention programs by collecting attendance, compliance, and performance information. This step may further include tracking member self-reported data, reviewing data collected through third party sensors and wearable electronic devices, and collecting health intervention program provider's evaluation and feedback. The computer implemented method may further include processing any received data from the member self-reported data and received data collected through the third party sensors and the wearable electronic devices and the feedback from one or more health intervention program providers.

The computer implemented method may further include using a machine learning process and received data from the member self-reported data and received data collected through the third party sensors and the wearable electronic devices as well as feedback from the one or more health providers and/or other parties, recalculating the initial score for the overall health score using a machine learning engine that provides a recalculated score that encourages attendance to one or more programs of the select programs that are underattended by the member. The method may further include providing an updated score for the overall health score of the member with an updated recommendations for which programs of the select programs to attend in the next period as well as recommendations for new programs from the one or more health intervention program. Further, the method may include using a the machine learning process to identify the less participated and underperformed health intervention programs with low adherence and underperformance, to remind medical providers of the less participated and underperformed health intervention programs in a next visit for the member, and to suggest to medical providers to change a weighting of health score incentives to a health intervention program or switch to a similar health intervention program that is easier to adhere to.

In another aspect, the method may include collecting program information regarding program type data, program specification data, target member group data, and health effect data. The method may further include aggregating program information, attendance, auto-detected performance, and trainer feedback data using the preventative care and health intervention application, wherein the calculated first score for the physical health of the member and the calculated first score for the mental health of the member is based in part on an evaluation of lab tests and imaging data, prescription drug data, medical condition data, medical history data, demographic data, and organ system function data.

In a non-limiting embodiment, the calculated first score for the social health of the member comprises evaluating a financial status, occupation, living environment, and social connectedness of the member. The method may further include unlocking access to additional health intervention programs or health care programs to assist the member in improving the overall health score. The method may further include rewarding the member with incentives provided through the preventative care and health intervention application if the overall health score is determined to improve on a scoring scale. In a non-limiting embodiment, the incentives comprise monetary compensation and crypto currencies or the incentives comprise redeemable points that can be used for travel, merchandise, gift cards, services, events, or donations.

Further, in a non-limiting embodiment, the health providers can assign extra weight to a select program of the selected programs in order to prioritize the select program in the overall health score.

In a non-limiting embodiment, the method may further include using a set of questions and applicant provided responses to the set of questions, screening an individual by automatically analyzing the applicant provided responses to the set of questions about the medical health of the applicant to detect a presence of a medical condition or other condition that excludes participation in the one or more preventative health care and health intervention programs, and responsive to detecting the presence of the medical condition or other condition that excludes participation, rejecting the applicant for participation in the one or more preventative health care and health intervention programs, wherein a medical provider can override the rejection of the applicant upon consideration of a total review of the applicant and entire medical history of the applicant and assessment of a level of fitness of the applicant for participation in the one or more preventative health care and health intervention programs.

The method may further include assigning points to the applicant provided responses to the set of questions based on a predetermined template and uniform scoring system; and totaling the points together for the member provided responses, and then providing the overall health score with breakdowns for the member wherein the overall health score includes scores related to the physical health, the mental health, and the social health of the member, further comprising adjusting the overall health score based on clinical intuition and input from a medical provider who has further performed risk stratification of the member's physical and mental health and analyzed a current health status of the member and a current lifestyle status of the member.

In a non-limiting embodiment, the present description further includes a system having a processor and a a system memory coupled to the processor and storing instructions configured to cause the processor to locally implement part of a preventative care and health intervention application in the system memory, including evaluate eligibility of an applicant for one or more preventative health care and health intervention programs. The system may further responsive to a determination that the application is eligible, enroll the applicant and convert the applicant to a member further comprising activating a profile of the member in the preventative care and health intervention application and gather a member's demographic and geographic data and medical history and other characteristic data by obtaining current and historical medical data associated with the member, wherein the medical history covers physical, mental, and social health history, assign one or more health providers, evaluate the member's overall health risks based on several factors comprising member medical history, family history, occupation, lifestyle, nutrition, daily activities, and health risks that relate to a physical health, a mental health, and a social health of the member, calculate an overall health score comprised of a calculated first physical health score of the member, a calculated first mental health score of the member, and a calculated first social health score of the member, and prescribe an initial set of programs for the member comprising select programs from the one or more preventative health care and health intervention programs with a goal to improve the overall health score as well as the calculated first physical health score of the member, the calculated first mental health score of the member, and the calculated first social health score of the member.

The system may further track progress of the member in following the select programs from the one or more preventative healthcare programs and health intervention programs. After a period of time, the system may also assemble together health intervention program attendance and performance data, characteristic data, health data, health score data, or any other relevant data related to the member from one or more databases to form an assembled dataset and select two or more variables from the assembled dataset, whereby the assembled dataset represents characteristics of the member, participation level in the select programs, and a change of health risks for the member. The system may also calculate a coefficient that represents an association between the participation and performance level in the select programs and the change of health risks for the member, wherein the coefficient is calculated from among at least one of the group comprising a covariance, a Pearson's correlation coefficient, a Spearman's correlation coefficient, a Kendall rank correlation, a Point-Biserial correlation, multiple correlation coefficient, linear regression coefficient, logistics regression coefficient or another relevant type of coefficient and generate one or more correlation matrices showing correlation coefficients between the health intervention program attendance and performance data, the characteristic data, the health data, the health score data, and/or any other relevant data related to the member. The system may also select an outstanding correlation coefficient that represents a positive correlation between the health intervention program attendance and performance data, the characteristic data, the health data, the health score data, and/or any other relevant data related to the member. The system may also return a list of recommended health intervention programs for preventative health providers to select from to recommend to the member and select an outstanding correlation coefficient that represents a negative correlation between the health intervention program attendance and performance data, the characteristic data, the health data, the health score data, and/or any other relevant data related to the member, and return a list of inadvisable health intervention programs for preventative health providers to dissuade the member from participating in.

Other aspects and advantages of the invention will be apparent from the following description and the appended claims.

BRIEF DESCRIPTION OF THE DRAWINGS

The preceding and following embodiments and descriptions are for illustrative purposes only and are not intended to limit the scope of this disclosure. Other aspects and advantages of this disclosure will become apparent from the following detailed description.

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

FIG. 2B depicts a table of criteria utilized to determine physical health scoring as part of the preventative care and health intervention application.

FIG. 2C depicts a table of criteria utilized to determine mental/emotional health scoring as part of the preventative care and health intervention application.

FIG. 2D depicts a table of criteria utilized to determine social health scoring as part of the preventative care and health intervention application.

DETAILED DESCRIPTION

As noted above, the current health care system is built for acute diseases. No comprehensive preventative care is available to help people assess health risks early on and to adjust lifestyles to prevent diseases based on clinical evidence. Annual checkups are the only preventative services available to the mass population, but annual checkups cannot be sufficient for delivering effective preventative care. Physicians have to cover a variety of exams in a short period of time including but not limited to medical histories, vital signs, physical exams, vaccines, screening, and preventative drugs, etc. The physicians and other medical staff have a very limited time available to educate patients on behaviors that can impact patients' health. The United States Preventive Services Task Force (USPSTF) is an independent panel of experts in primary care and prevention that systematically reviews the evidence of effectiveness and develops recommendations for clinical preventive services." Notably, the USPSTF recommends multiple contacts including either individual or group counseling sessions over a long period of time to prevent many diseases, but the traditional clinical setting cannot meet these recommendations in either scope or duration. For example, behavioral counseling interventions for reducing health risks for cardiovascular diseases usually include either individual or group counseling sessions up to a year. For another example, studies have shown that multiple group or individual counseling sessions that last at least two or more hours show effectiveness in reducing sexually transmitted infections. All these programs cannot be fully delivered in traditional clinical settings, nor do they fit the traditional health insurance's reimbursement model.

The present description includes one or more non-limiting embodiments to assist people stay health and optimize their health through the different stages of life. The one or more embodiments describe herein a preventative care and health intervention application that can assist members to engage in healthy activities and lifestyle choices that can improve their physical, mental, and social health.

Further details and information about the one or more illustrative embodiments for a preventative care and health intervention application available for use on one's computing device is provided below in association with the corresponding Figures.

Figure 1A:
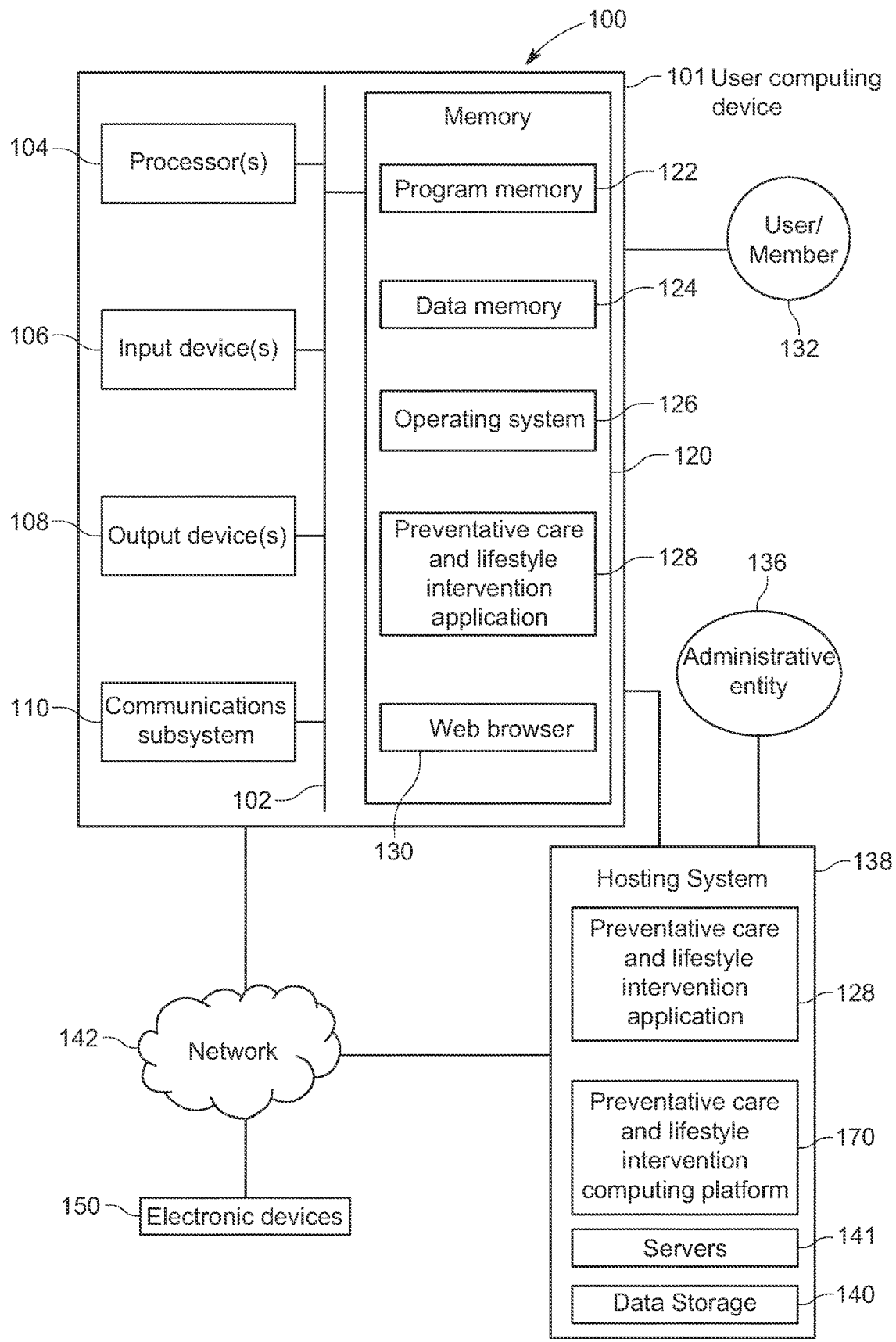
FIG. 1A depicts an exemplary computer system incorporating various components of an exemplary computing device and network in accordance with one or more illustrative embodiment.

Turning to FIG. 1, FIG. 1 illustrates an exemplary system for one or more computing devices and the various exemplary components that may be employed in practicing one or more non-limiting embodiments of the invention as described herein. Computing device 100 may be any type of computing device known or to be created in the future. This may include, without limitation, fixed in place computers, such as desktop computers or mobile computing devices. Mobile computing devices may include, but are not limited to, laptop computers, smartphones and mobile phones, tablets, wearable electronic computing devices such as watches or glasses, or any other type of mobile electronic, computing device.

FIG. 1 provides a schematic illustration of one embodiment of a computing device 100 that can perform the methods provided by the various other listed embodiments, as described herein, and/or can function as the host computer system, a remote kiosk/terminal, a point-of-sale device, a mobile device, a set-top box and/or a computer system. FIG. 1 is meant only to provide a generalized illustration of various components, any or all of which may be utilized as appropriate. FIG. 1, therefore, broadly illustrates how individual system elements may be implemented in a relatively separated or relatively more integrated manner.

Computing device 100 may be any type of information handling system, including, but not limited to, any type of computing device as noted above. To reiterate, this may include small handheld devices, such as handheld computer/mobile telephones or may include large mainframe systems, such as a mainframe computer. Further examples of handheld computing devices may include personal digital assistants (PDAs), personal entertainment devices, such as MP3 players, portable televisions, and compact disc players. Other examples of computing devices 100 may include, but are not limited to, laptops, notebooks, workstation computers, personal computer systems, as well as servers (e.g., servers 141). Computing devices 100 can be used by various parties described herein and may be connected on a computer network, such as computer network 142. Types of computer networks that can be used to interconnect the various information handling systems may include, but are not limited to, Local Area Networks (LANs), Wireless Local Area Networks (WLANs), the Internet (e.g., World Wide Web), the Public Switched Telephone Network (PSTN), other wireless networks, and any other network topology that can be used to interconnect the information handling systems.

The computing device 100 is shown comprising hardware elements that can be electrically coupled via a bus 102 (or may otherwise be in communication, as appropriate). The hardware elements of computing device 100 may include one or more processors 104, including without limitation one or more general-purpose processors and/or one or more special-purpose processors (such as digital signal processing chips, graphics acceleration processors, and/or the like). Computing device 100 may further include one or more input devices 106, which can include without limitation one or more cameras, sensors (including inertial sensors), a mouse, a keyboard and/or the like, which may be utilized in the implementation of preventative care and health intervention application 128.

In addition to the above, computing device 100 may include one or more output devices 108 such as the device display. Furthermore, in some embodiments, an input device 106 and an output device 108 of computing device 100 may be integrated, for example, in a touch screen or capacitive display as commonly found on mobile computing devices as well as desktop computers and laptops.

Processors 104 may have access to a memory such as memory 120. Memory 120 may include one or more of various hardware devices for volatile and non-volatile storage and may include both read-only and writable memory. For example, memory 120 may comprise random access memory (RAM), CPU registers, read-only memory (ROM), and writable non-volatile memory, such as flash memory, hard drives, floppy disks, CDs, DVDs, magnetic storage devices, tape drives, device buffers, and so forth. A memory 120 is not a propagating signal divorced from underlying hardware; a memory is thus non-transitory. Memory 120 may include program memory such as program memory 122 capable of storing programs and software, such as an operating system 126, preventative care and health intervention application 128, and other computerized programs or application programs. Memory 120 may also include data memory such as data memory 124 that may include database query results, configuration data, settings, user options or preferences, etc., which may be provided to program memory 122 or any element of computing device 100.

The computing device 100 may further include (and/or be in communication with) one or more non-transitory storage devices, which can comprise, without limitation, local and/or network accessible storage, and/or can include, without limitation, a disk drive, a drive array, an optical storage device, a solid-state storage device such as a random-access memory ("RAM") and/or a read-only memory ("ROM"), which can be programmable, flash-updateable and/or the like. Such storage devices may be configured to implement any appropriate data storage, including without limitation, various file systems, database structures, and/or the like. Device storage may be used in a number of embodiments discussed herein. Further, the storage devices may be non-volatile data storage devices in one or more non-limiting embodiments. Further, computing device 100 may be able to access removable nonvolatile storage devices that can be shared among two or more information handling systems (e.g., computing devices) using various techniques, such as connecting the removable nonvolatile storage device to a USB port or other connector of the information handling systems.

The computing device 100 might also include a communications subsystem 110, which can include without limitation a modem, a network card (wireless or wired), an infrared communication device, a wireless communication device and/or chipset (such as a Bluetooth™ device, an 802.11 device, a WIFI device, a WiMAX device, cellular communication facilities, etc.), and/or the like. The communications subsystem 110 may permit data to be exchanged with a network (e.g., such as network 186), other computer systems, and/or any other devices.

The computing device 100 also can comprise software elements, shown as being currently located within the memory 120, which in some instances may include an operating system 126, device drivers, executable libraries, and/or other code, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer). In an aspect, then, such code and/or instructions can be used to configure and/or adapt computing device 100 to perform one or more operations in accordance with the described methods.

A set of these instructions and/or code might be stored on a computer-readable storage medium, such as the storage device(s) described above. In some cases, the storage medium might be incorporated within a computer system, such as computing device 100. In other embodiments, the storage medium might be separate from computing device 100 (e.g., a removable medium, such as a compact disc or USB stick), and/or be provided in an installation package, such that the storage medium can be used to program, configure, and/or adapt a general-purpose computer with the instructions/code stored thereon. These instructions might take the form of executable code, which is executable by the computing device 100 and/or might take the form of source and/or installable code, which, upon compilation and/or installation on the computing device 100 (e.g., using any of a variety of generally available compilers, installation programs, compression/decompression utilities, etc.) then takes the form of executable code.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Some embodiments may employ a computer system (such as the computing device 100) to perform methods in accordance with the disclosure. For example, some or all of the procedures of the described methods may be performed by the computing device 100 in response to one or more processors 104 executing one or more sequences of one or more instructions (which might be incorporated into the operating system 126 and/or other code contained in the memory 120). Such instructions may be read into the memory 120 from another computer-readable medium, such as one or more of the storage devices(s). Merely by way of example, execution of the sequences of instructions contained in the memory 120 may cause the one or more processors 104 to perform one or more procedures of the methods described herein.

The terms "machine-readable medium" and "computer-readable medium," as used herein, refer to any medium that participates in providing data that causes a machine to operate in a specific fashion. In an embodiment implemented using the computing device 100, various computer-readable media might be involved in providing instructions/code to the one or more processors 104 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media may include, for example, optical and/or magnetic disks which may be an example of storage devices. Volatile media may include, without limitation, dynamic memory, which may be a type of memory included in memory 120. Transmission media may include, without limitation, coaxial cables, copper wire and fiber optics, including the wires that comprise the bus 102, as well as the various components of the communications subsystem 110 (and/or the media by which the communications subsystem 110 provides communication with other devices). Transmission media can also take the form of waves (including without limitation radio, acoustic and/or light waves, such as those generated during radio-wave and infrared data communications).

Common forms of physical and/or tangible computer-readable media include, for example, a floppy disk, a flexible disk, hard disk, magnetic tape, or any other magnetic medium, a CD-ROM, any other optical medium, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of computer-readable media may be involved in carrying one or more sequences of one or more instructions to the processor(s) 104 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 100. These signals, which might be in the form of electromagnetic signals, acoustic signals, optical signals and/or the like, are all examples of carrier waves on which instructions can be encoded, in accordance with various embodiments of the invention.

The communications subsystem 110 (and/or components thereof) generally will receive the signals, and the bus 102 then might carry the signals (and/or the data, instructions, etc. carried by the signals) to the memory 120, from which the one or more processors 104 retrieves and executes the instructions. The instructions received by the memory 120 may optionally be stored on a non-transitory storage device either before or after execution by the processor(s) 104.

In one or more embodiments, computing device 100 is in communication with one or more networks, such as network 142. Network 142 may include a local area network (LAN), such as a company Intranet, a metropolitan area network (MAN), or a wide area network (WAN), such as the Internet or World Wide Web. Network 142 may be a private network, a public network, or a combination thereof. Network 142 may be any type of network known in the art, including a telecommunications network, a wireless network (including Wi-Fi), and a wireline network. Network 142 may include mobile telephone networks utilizing any protocol or protocols used to communicate among mobile digital computing devices (e.g., computing device 100), such as GSM, GPRS, UMTS, AMPS, TDMA, or CDMA. In one or more non-limiting embodiments, different types of data may be transmitted via network 142 via different protocols. In further non-limiting other embodiments, computing device 100 may act as a standalone device or may operate as a peer machine in a peer-to-peer (or distributed) network environment.

Network 142 may further include a system of terminals, gateways, and routers. Network 186 may employ one or more cellular access technologies including but not limited to: 2nd (2G), 3rd (3G), 4th (4G), 5th (5G), LTE, Global System for Mobil communication (GSM), General Packet Radio Services (GPRS), Enhanced Data GSM Environment (EDGE), and other access technologies that may provide for broader coverage between computing devices if, for instance, they are in a remote location not accessible by other networks.

In one or more non-limiting embodiments, a computing device, such as computing device 100 may include a web browser such as web browser 130. Web browser 130 may be any type of web browser known in the art that may be used to access one or more web applications (e.g., preventative care and health intervention application 128) on user computing devices 100 or the like. Web applications are applications that are accessible by network 142 and may be located on the Internet or World Wide Web. Web browser 130 may include a variety of hardware, software, and/or firmware generally operative to present a web application to a user via a display device 108 (e.g., touchscreen or other type of monitor or display device) on a computing device. Examples of suitable web browsers include, but are not limited to, MICROSOFT EXPLORER, MOZILLA FIREFOX, and APPLE SAFARI. Web browser 130 may be previously installed by the manufacturer or company associated with the computing device 100, or alternatively, may be downloaded onto computing device 100 or any other computing device. Web browser 130 may be stored in a separate storage device and/or memory 120.

In one or more non-limiting embodiment, preventative care and health intervention application 128 may be a comprehensive software program or module configured to counsel a member on healthy habits and activities to prevent illnesses, diseases, and other negative conditions that may affect a user's physical, mental or social health. Additionally, the preventative care and health intervention application 128 may coordinate and facilitate access for members to one or more health intervention/improvement programs. Further, the preventative care and health intervention application 128 may provide monitoring of a member by one or more medical providers to monitor the member's health and attendance of preventative care and health intervention programs.

Further, the preventative care and health intervention application 128 may provide a unique overall health score when the member is first initiated that is broken down into initial health scores for the member's physical health, mental health, and social health based on a health evaluation result including but not limited to the member's current health conditions, family history healthy habits, and previous medical diagnosis or treatment. As the member participates in one or more preventative health care and health intervention programs, the providers and program directors monitor and track the member's attendance and performance. The scoring system can be used to evaluate and provide an updated overall health score to the member, with updated health scores that reflect the change of health status from Health Evaluation, performance in the Health intervention Programs, and impacts from other Medical Interventions in the physical, mental, and social health dimensions of the member after having participated in the one or more preventative counseling services, health intervention programs, and medical interventions offered and managed by the administrative entity 136 associated with the preventative care and health intervention program 128 inside or outside of the program network. Incentives and rewards are further offered and provided as part of the preventative care and health intervention application 128 to reward and/or incentivize members to participate in the preventative counseling services, health intervention programs, or medical interventions and to improve their health scores over the range of scores provided for their physical, mental, and social health. The system 100 further integrates modules and engines that provide predictive analytics to assist in the health risk assessment (HRAs) and risk stratification analysis component of the health scoring system as further described below. Accordingly, the preventative care and health intervention application 128 can calculate health risks and predicting health trajectories based on assessment of the current health status of the member, the current lifestyle status of the member, their compliance and performance in the Health Intervention Programs, if they have gone through any medical interventions in the physical, mental, and social dimensions and further based on predictive analytics of all the above components and dimensions integrated with the preventative care and health intervention application.

In one or more non-limiting embodiments, preventative care and health intervention application 128 may be implemented as a web service. As known in the art, a web service may be a software module or software program (e.g., preventative care and health intervention application 128) that is designed to implement a set of tasks that is accessible from multiple computing devices, such as computing device 100 over a network, such as network 142. In particular, preventative care and health intervention application 128 may be implemented as a web service accessible using the World Wide Web as the connecting network 142, although any alternative type of network may be used. Preventative care and health intervention application 128, when implemented as a web service, can be searched by any user (e.g., user/member/patient 132) using web browser 130. Preventative care and health intervention application 128 when implemented as a web service can be searched for over the network 142 using the input devices 106 of a computing device and can also be invoked accordingly. Further, preventative care and health intervention application 128 when invoked as a web service would be able to provide functionality to the client or user which invokes that web service.

When preventative care and health intervention application 128 is implemented as a web service, a client or party may invoke a series of web service calls via requests to one or more servers 141 that are part of the hosting system 138 which would host the actual web service. In one or more non-limiting embodiments, hosting system 138 may be a cloud-based type hosting system. "Cloud-based" is a term that refers to applications, services, or resources (e.g., preventative care and health intervention application 128) made available to users on demand via a network, such as network 142, from a cloud computing provider's server. In one non-limiting embodiment, administrative entity 136 may be the cloud computing provider and may use servers 141 to provide access to preventative care and health intervention application 128.

Hosting system 138 may include data storage systems 140 that can provide access to stored data by applications running on computing devices (e.g., 100) that may be geographically separate from each other, provide offsite data backup and restore functionality, provide data storage to a computing device with limited storage capabilities, and/or provide storage functionality not implemented on a computing device (e.g., 100).

The hosting system 138 may be a service that can be implemented as a web service, in one or more non-limiting embodiments, with a corresponding set of Web Service Application Programming Interfaces (APIs). The Web Service APIs may be implemented, for example, as a Representational State Transfer (REST)-based Hypertext Transfer Protocol (HTTP) interface or a Simple Object Access Protocol (SOAP)-based interface. Any programming languages may be used to create or operate preventative care and health intervention application 128 as a web service, including, but not limited to .Net, Java, and XML. Further, preventative care and health intervention application 128 as a web service may use standardized industry protocol for the communication and may include well-defined protocols, such as Service Transport, XML Messaging, Service Description, and Service Discovery layers in the web services protocol stack.

For instance, the hosting system 138 can be implemented such that client applications (for example, executing on computing device 100) can store, retrieve, or otherwise manipulate data objects in the hosting system 138. The hosting system 138 can be implemented by one or more server devices 141, which can be implemented using any type of computing device.

Figure 1B:
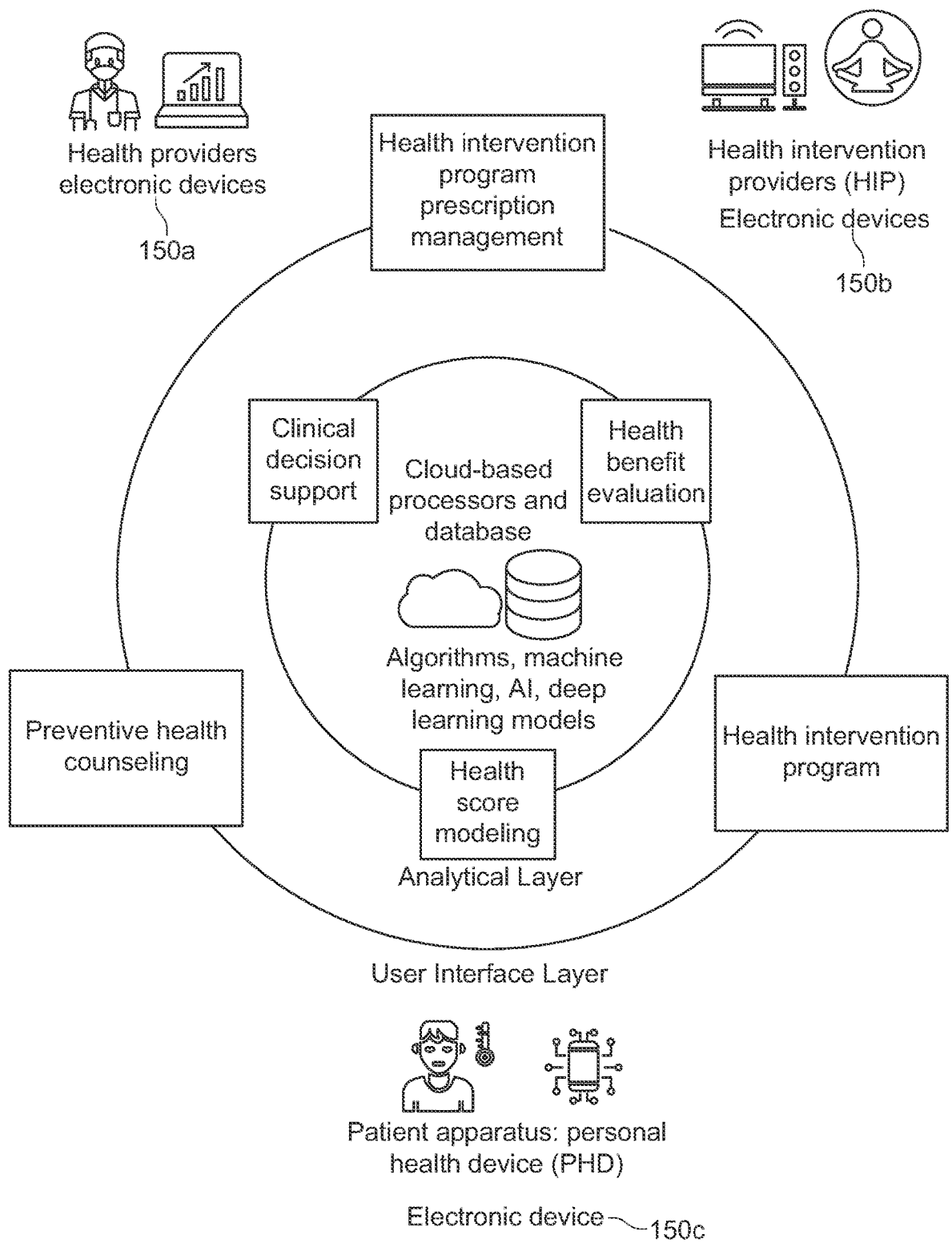
FIG. 1B depicts a pictorial illustration of an example operating environment in which one or more aspects of the preventative care and health intervention computing program and system described herein may be implemented.
Figure 1C:
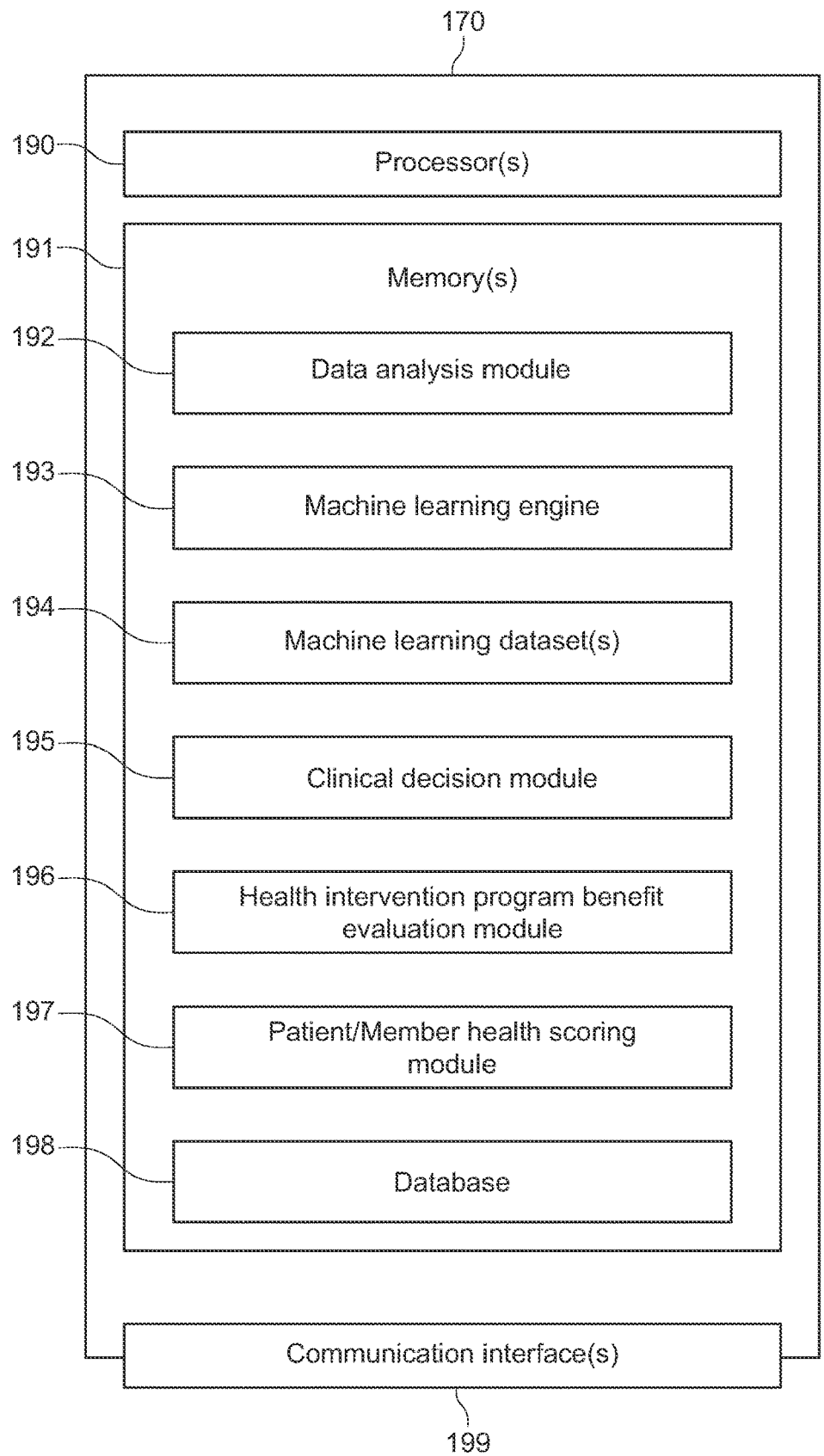
FIG. 1C depicts a block diagram for one or more components of a machine learning engine for the preventative care and health intervention computing program.

The hosting system 138 may further include a preventative care and health intervention computing platform 170, which is further elaborated upon in FIG. 1C. Notably, the preventative care and health intervention computing platform 170 may be configured to host and/or execute a machine learning engine, such as machine learning engine 193, to provide automated data analysis functions for the preventative care and health intervention application 128. This may include monitoring and receiving and/or assembling data from datasets that relate to a member 132's health program attendance data, performance data, characteristic data for programs, including health intervention programs 203, as shown and described with respect to FIG. 2A, and other relevant data related to a member 132. The term "member" as used herein may also interchangeably be referred to as "patient." The term "health intervention program" may also be interchangeable with "lifestyle intervention program" or "health intervention application" and so on in this application.

Figure 2A:
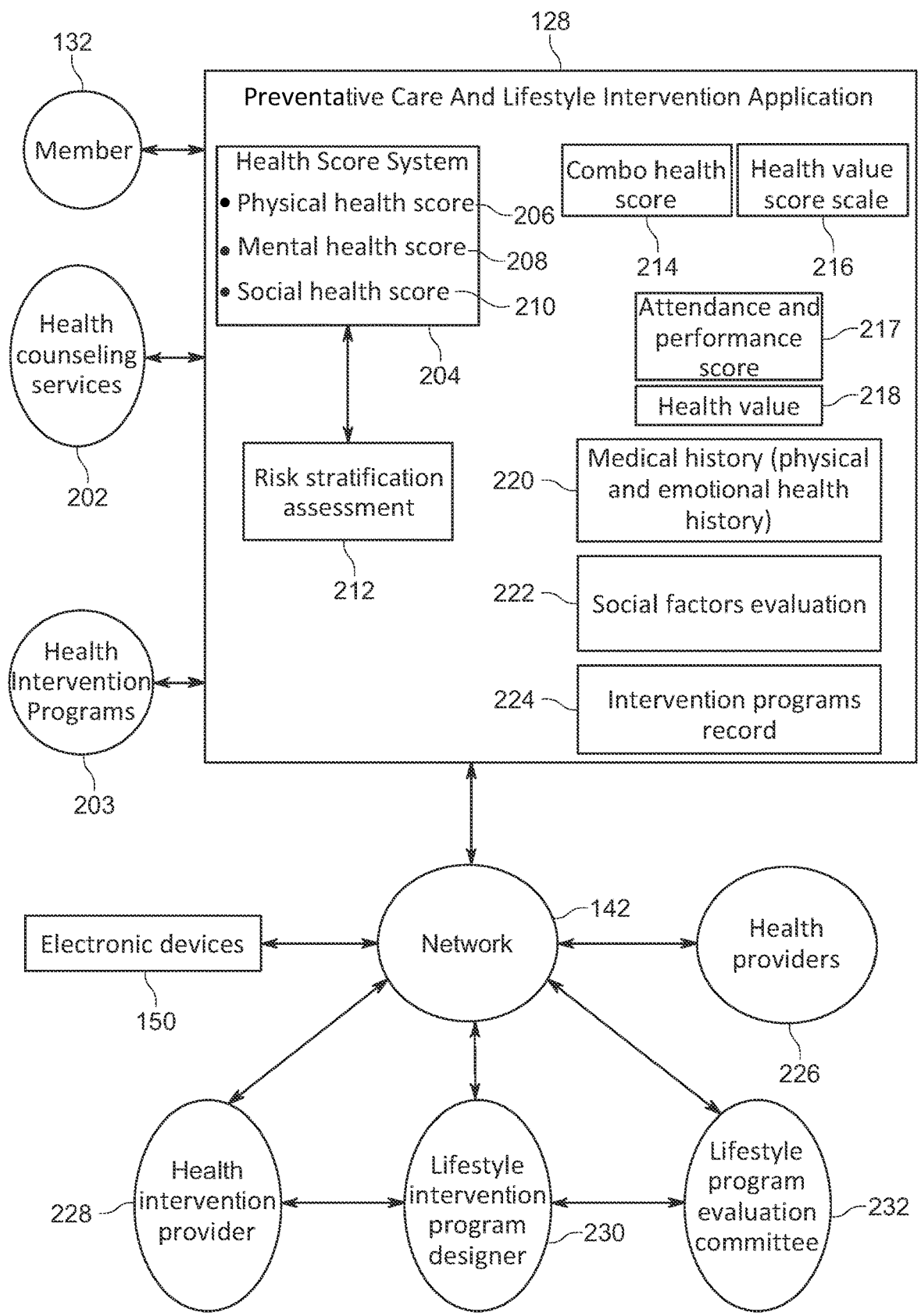
FIG. 2A depicts a block diagram of components of a preventative care and health intervention application and system.

The systems associated with the preventative care and health intervention computing platform 170 may be one or more servers, applications executing on one or more devices, other computing platforms, and the like. The systems, in at least some examples, may be systems configured to collect data from one or more databases related to a member 132 and/or health providers 226 and/or health intervention program designers 230 as shown in FIG. 2A, as well as from various electronic devices 150. In particular, the data may be received from hundreds or thousands electronic devices 150 and may be analyzed by the preventative care and health intervention computing program 170.

In one or more non-limiting embodiments, administrative entity 136 is the provider and creator of preventative care and health intervention application 128. Administrative entity 136 may provide the application programming interface (e.g., preventative care and health intervention application 128) for use by user/member 132. Administrative entity 136 may be able to manipulate and alter preventative care and health intervention application 128 to affect the operation and maintenance of preventative care and health intervention application 128 on server(s) 141 and as stored on one or more data storage devices 140 that are part of the hosting system 138. While administrative entity 136 is depicted as a single element communicating over network 142 and through the hosting system 138, it is noted that administrative entity 136, in one or more non-limiting embodiments, may be distributed over network 142 in any number of physical locations.

In one or more non-limiting embodiments, preventative care and health intervention application 128 may alternatively be a downloadable software module that is capable of being stored directly on a computing device, such as computing device 100, rather than acting as a web service accessible through a computing device's web browser 130. Accordingly, any user may be able to download and store preventative care and health intervention application 128 on computing device 100 as a computer-based application and software module that runs using the working engines and modules on the computing device. In some embodiments, preventative care and health intervention application 128 may be preinstalled on computing device 100 or any other computing device by the manufacturer or designer or other entity. Preventative care and health intervention application 128 may be innate, built into, or otherwise integrated into existing platforms such as, without limitation thereto, a website, third-party program, iOS™, Android™ Snapchat™, Getty Images™, Instagram™, Facebook™, or any other platform capable transmitting, receiving, and presenting data.

Preventative care and health intervention application 128 may be stored on computing device 100 or any other computing devices and may also be stored or otherwise accessible by one or more servers 180 over network 142 by any party. The storage devices may include a non-transitory computer readable medium including instructions, which when executed by a computer or processor (such as processors 104) may cause the computer or processor to perform operations to implement preventative care and health intervention application 128. Additionally, or alternatively, preventative care and health intervention application 128 may be a software application that is downloadable and usable from any type of mobile computing device 100.

Electronic devices 150 may include one or more medical devices, such as, for example, an infusion device, a sensing device, a monitoring device, and/or the like. Additionally, the electronic devices 150 may include any number of non-medical client electronic devices, such as, for example, a mobile phone, a smartphone, a tablet computer, a smart watch, or other similar mobile electronic device, or any sort of electronic device capable of communicating with the computing device 101 via the network 142 such as a laptop or notebook computer, a desktop computer, or the like. One or more of the electronic devices 150 may include or be coupled to a display device, such as a monitor, screen, or another conventional electronic display, capable of graphically presenting data and/or information pertaining to the physiological condition of a patient. Additionally, one or more of the electronic devices 150 also includes or is otherwise associated with a user input device 106, such as a keyboard, a mouse, a touchscreen, a microphone, or the like, capable of receiving input data and/or other information from a user of the electronic device 150.

In exemplary embodiments, one or more of the electronic devices 150 transmits, uploads, or otherwise provides data or information to the computing device 101 for processing at the computing device 101 and/or storage in the data storage 140. For example, when an electronic device 150 is realized as a sensing device, monitoring device, or other device that includes sensing element is inserted into the body of a patient or otherwise worn by the patient to obtain measurement data indicative of a physiological condition in the body of the patient, the electronic device 150 may periodically upload or otherwise transmit the measurement data to the computing device 102. In other embodiments, electronic device 150 may be utilized by a patient to manually define, input or otherwise track relevant data associated with the user 132's health, including physical, mental health, and social health, and to transmit, upload, or otherwise provide such event log data to the computing device 101.

As shown in FIG. 1, computing device 100 may belong to a user referred to in FIG. 1 such as user 132 who is also a member/patient 132 as shown in FIG. 2A. User 132 may be a user that intends to access preventative care and health intervention application 128 using his or computing device 100 to participate in one or more preventative care and/or health intervention programs as also shown in FIG. 2A.

As noted above, in one non-limiting embodiment, preventative care and health intervention application 128 may be implemented as a web service as described above. Further information about other components of preventative care and health intervention application 128 are included below with respect to FIG. 2A-FIG. 9.

Figure 7:
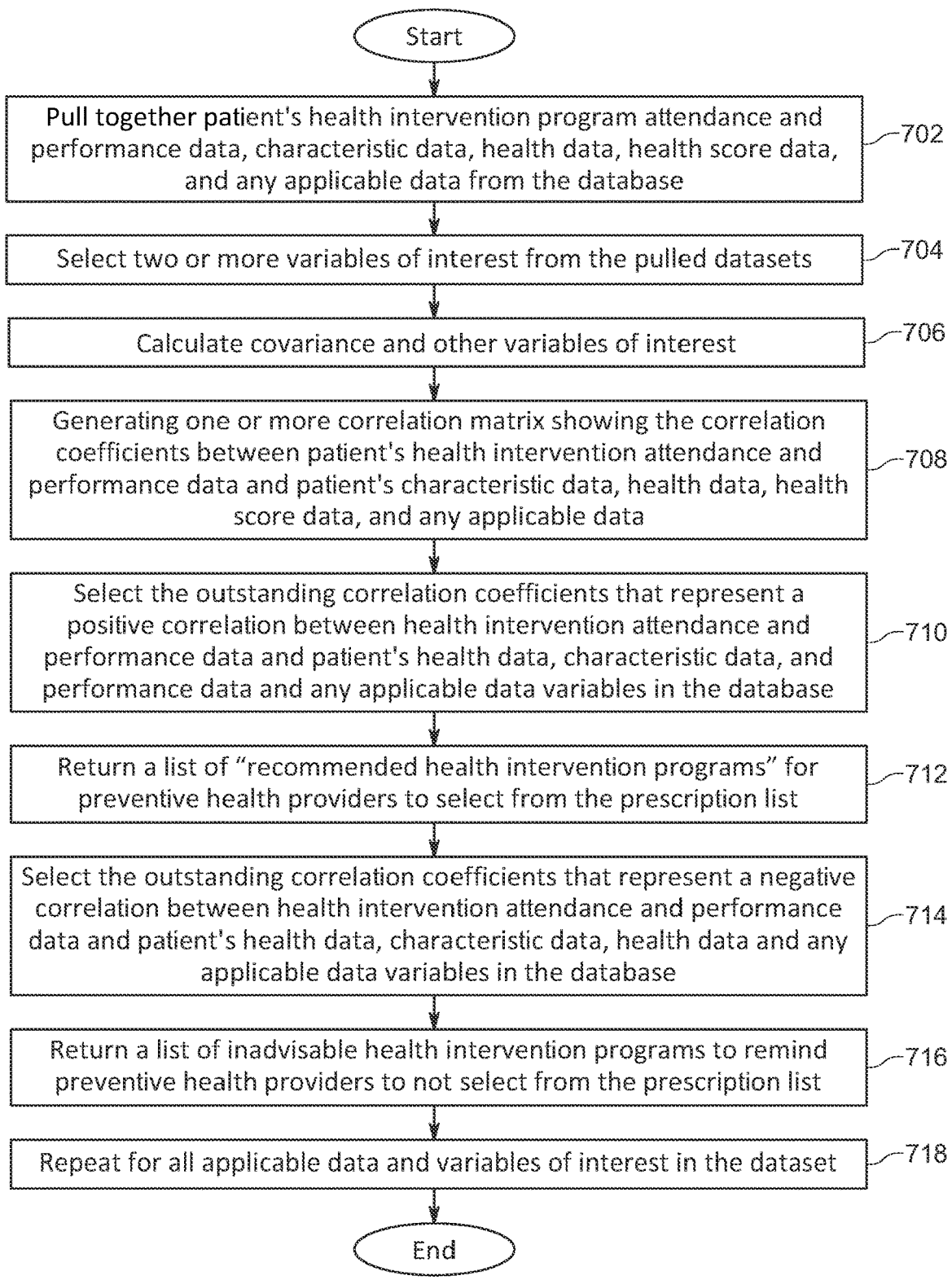
FIG. 7 depicts an exemplary flowchart for a clinical decision supporting module for medical providers to use to best fit a member's health and fitness goals within a period of time.
Figure 8:
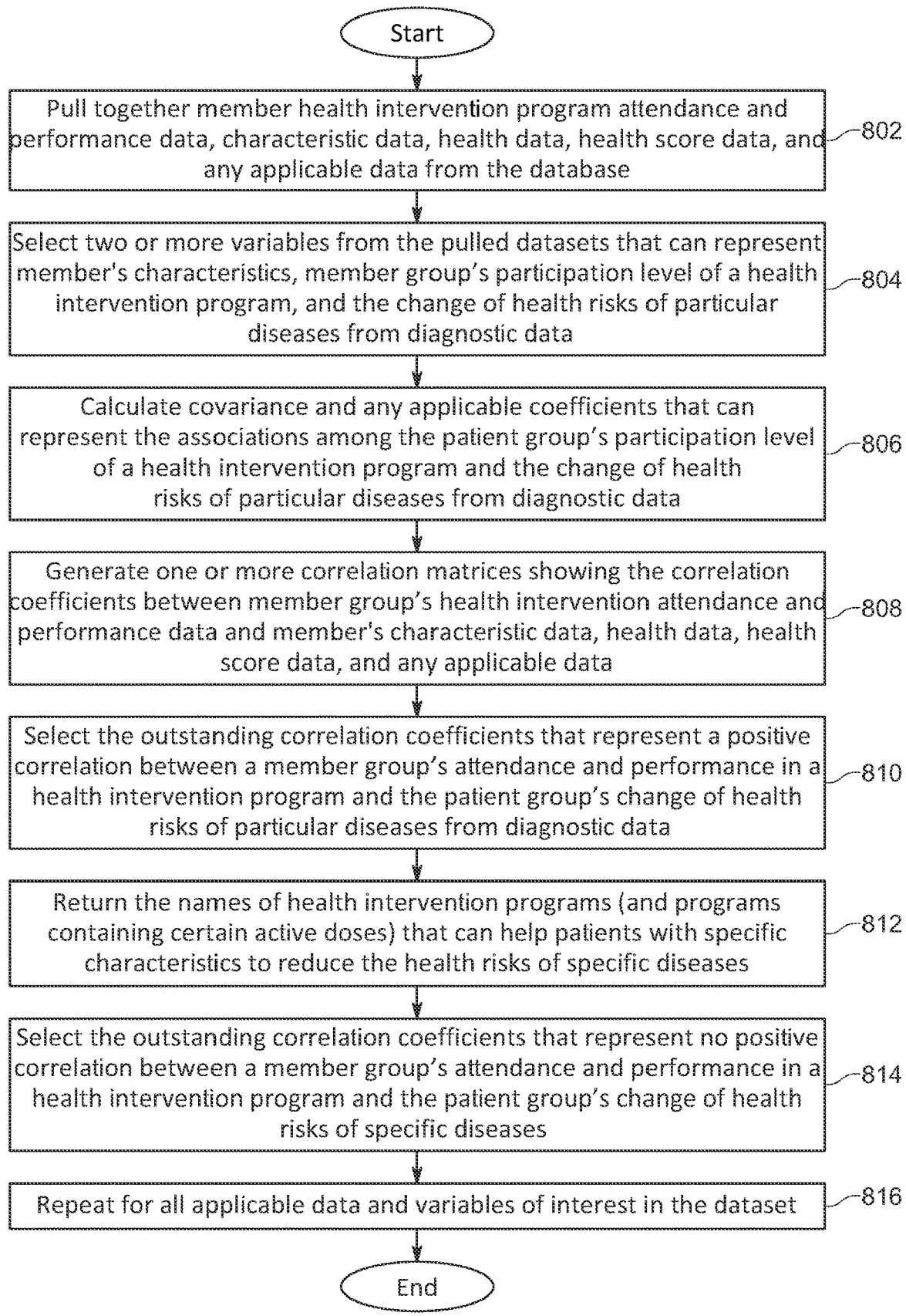
FIG. 8 depicts an exemplary flowchart for identifying the potential health effects of a health intervention program on a patient group and suggesting potential changes in a program's design to the health intervention program providers.
Figure 9:
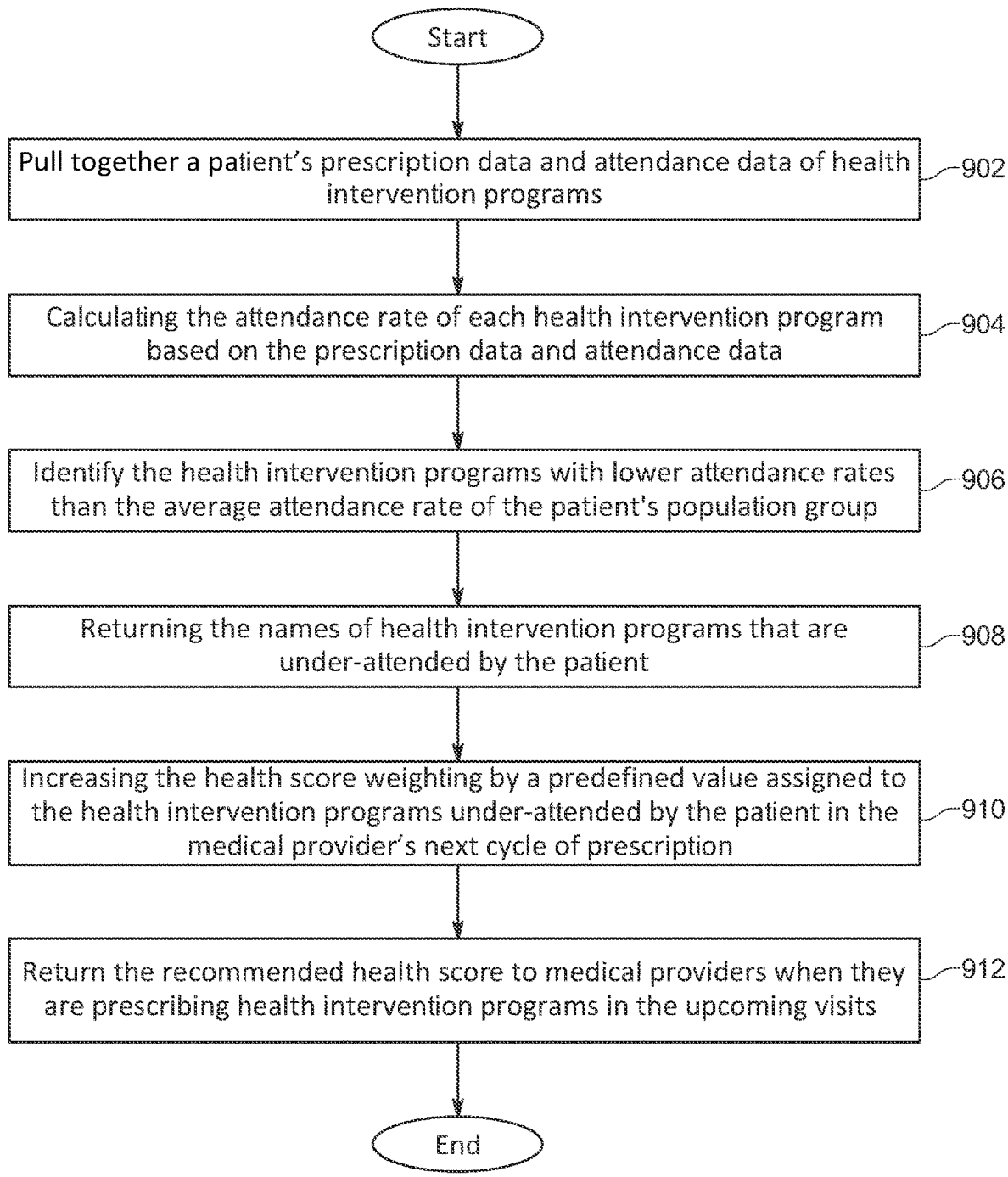
FIG. 9 depicts an exemplary flowchart for a method for scoring health intervention programs in an effort to incentive a member to adhere to health intervention programs.

FIG. 1B depicts an illustration of one or more aspects and components of the preventative care and health intervention application 128. In a non-limiting embodiment, the preventative care and health intervention application 128 may include a system for health intervention program prescription management. Using a number of algorithms, machine learning, artificial intelligence (AI), and deep learning models, the system 128 and/or system 170 may utilize cloud base processors and databases to provide clinical decision support (e.g., as shown in FIG. 7), health benefit evaluation (e.g., as shown in FIG. 8), and health score modeling (e.g., as shown in FIG. 9). There may be a number of analytical layers and analysis provided by the system 128 and/or system 170 to monitor and improve the analysis components of the clinical decision support, health benefit evaluation, and health score modeling. In a non-limiting embodiment, the cloud based processors and databases may utilize data pulled from the preventative care and health intervention application 128 from one or more electronic devices, including from the electronic devices 150a of the health providers 226, the electronic devices 150b of the health intervention providers 228, and/or the electronic devices 150c of the members 132 (who may also be referred to as patients).

FIG. 1C provides a block diagram for further details regarding the preventative care and health intervention computing platform 170. In a non-limiting embodiment, the preventative care and health intervention computing platform 170 may include one or more processors 190, memory 191, and a communication interface 199. A data bus may interconnect processors 190, memory 191, and the communication interface 199. The communication interface 199 may be a network interface configured to support communication between the preventative care and health intervention computing platform 170 and one or more networks 142 (which may be private networks, public networks, or the like). Memory 191 may include one or more program modules having instructions that when executed by processor(s) 190 cause the preventative care and health intervention computing platform 170 to perform one or more functions described herein and/or one or more databases that may store and/or otherwise maintain information which may be used by such program modules and/or processor(s) 190. In some instances, the one or more program modules and/or databases may be stored by and/or maintained in different memory units of computing platform 170 and/or by different computing devices that may form and/or otherwise make up computing platform 170.

For example, memory 191 may have, store, and/or include a data analysis module 192. Data analysis module 192 may store instructions and/or data that may cause or enable the computing platform 170 to receive, store and/or analyze data from one or more systems, devices, applications, or the like, being monitored by or transmitting data to the computing platform 170. The data analysis module 192 may receive, for example, data related to a member 132 from a number of sources, including the electronic devices 150a-150c shown in FIG. 1C, and the like. In some examples, the data may be segregated into portions. The data may relate to characteristic data of the health intervention or health intervention programs 203, health data, diagnostic data, performance data, attendance data by a member 132, a program name, type, amount/intensity, health values, prescription data, and any other applicable data. The data analysis module 192 may receive and analyze the data that may be used to (e.g., by machine learning engine 193) to generate one or more machine learning datasets 194.

Additionally, or alternatively, the data analysis module 192 may receive data from one or more electronic devices 150a-150c and/or servers 141 or data storage 140 and may compare the data to one or more machine learning datasets 194. The comparison data may be used to generate one or more recommendations for a clinical decision support process (e.g., as shown in FIG. 7), health intervention program (e.g., as shown in FIG. 8), and/or a health score modeling (e.g., as shown in FIG. 9).

Memory 191 may further have, store and/or include a machine learning engine 193 and machine learning datasets 194. Machine learning engine 193 and machine learning datasets 194 may store instructions and/or data that cause or enable the preventative care and health intervention computing platform 170 to determine or predict, in real-time and based on received data, advisable or inadvisable or recommended and not recommended health intervention programs 203 for a member 132 (e.g., for the clinical decision support process as shown in FIG. 7 or the health intervention program as shown in FIG. 8), or a recommended health score (e.g. for the health scoring modeling as shown in FIG. 9). In a non-limiting embodiment, there may be a clinical decision module 195 associated with the clinical decision support process shown in FIG. 7 that is also part of the preventative care and health intervention application 128. Further, there may be a health intervention program benefit evaluation module 196 associated with the preventative care and health intervention application 128 and associated with the health intervention program analysis shown in FIG. 8. Further, there may be a patient health scoring module 197 associated with the analysis and process for a health scoring model as shown in FIG. 9 also.

The preventative care and health intervention application 170 may further include one or more databases 198 that may store data associated with member 132's data including medical history 220, social factors evaluation 222, intervention programs record 224, and/or health intervention programs 203.

The machine learning engine 193 may receive data from a plurality of sources and, using one or more machine learning algorithms, may generate one or more machine learning datasets 194. Various machine learning algorithms may be used without departing from the invention, such as supervised learning algorithms, unsupervised learning algorithms, regression algorithms (e.g., linear regression, logistic regression, and the like), instance based algorithms (e.g., learning vector quantization, locally weighted learning, and the like), regularization algorithms (e.g., ridge regression, least-angle regression, and the like), decision tree algorithms, Bayesian algorithms, clustering algorithms, artificial neural network algorithms, and the like. Additional or alternative machine learning algorithms may be used without departing from the invention. In some examples, the machine learning engine 193 may analyze data to identify patterns of activity, sequences of activity, and the like, to generate one or more machine learning datasets 194. Additionally, or alternatively, the machine learning engine 193 may analyze a frequency of issue occurring. For instance, the machine learning engine 193 may analyze data to determine whether a frequency of a particular issue, behavior or indication for a particular member 132 and any identifying characteristics associated with the particular issue as well as characteristics of the member 132. This information may be used to generate one or more machine learning datasets 194.

The machine learning datasets 194 may be used to predict and recommend calculated initial and/or updated scores for the health score system 204, including the physical health score 206, mental health score 208, and social health score 210, as well as for an overall health score in a non-limiting embodiment.

Although the various modules of the computing platform 170 are described separately, functionality of the various modules may be combined and/or may be performed by a single device or multiple computing devices in communication without departing from the invention.

Turning to FIG. 2A, FIG. 2A provides a block diagram of exemplary components of the preventative care and health intervention application 128. Preventative care and health intervention application 128 may have multiple facets and sub-modules to implement its integrative, comprehensive services. As noted above, the traditional health care system is not designed to and is unable to fully address providing preventative care and health intervention counseling and programs that can help people avoid and prevent many chronic diseases and infectious diseases, manage and control mental and emotional disorders, improve their social wellness, and maintain their health on multiple levels. The traditional model revolves around visits to a clinic, hospital, or other medical service location, prescribing medicine. Rarely, does the traditional model include making recommendations for lifestyle changes, and is lacking an established model or system for tracking such lifestyle changes are occurring or that the member's health is improving.

The preventative care and health intervention application 128, as described herein in one or more non-limiting embodiments, may be particularly adept at offering multiple service tiers that integrate online preventative health counseling services with ongoing health intervention programs to help prevent diseases proactively. In a non-limiting embodiment, the applicants that initially apply and are enrolled/accepted to participate in the preventative care and health intervention application 128 may be members 132. In other words, the administrative entity 136 shown in FIG. 1 may be an entity that provides the management and oversight of the preventative care and health intervention application 128, as well as membership services to its members 132. Accordingly, the member 132 when enrolled may have multiple levels of services available to him or her based on the subscription or membership package or services chosen by the member 132. In a non-limiting embodiment, the members 132 can pay a monthly/annual membership fee to access a network of highly beneficial health services that can benefit not just the physical and mental health of the member 132, but other aspects as well, including the social well-being of the member 132. The social well-being of the member 132 may include connectedness to family and friends, meaningful relationships, stable job, connectedness to community, healthy living conditions, healthy hobbies, and healthy financial status, as well as many other factors.

In a first tier, the preventative care application and health intervention application 128 may offer a medical platform providing personalized preventative care services. Accordingly, the preventative care and health intervention 128, in a non-limiting embodiment, incorporates health counseling services 202 focused on evaluating medical status and conditions of the members 132 and may include medical related activities and services like traditional primary care services. Members/Patients 132 can seek advice from health providers 226. In a non-limiting embodiment, health providers 226 may be any credentialed, licensed, authorized to practice individual that can counsel on medical conditions and illnesses. Examples of health providers 226 include physicians, nurse practitioners, physician assistants, or any qualified medical professionals both domestically and internationally. The patients 132 can seek advice from health providers 226 on behavior change, lifestyle, immunization, chemoprophylaxis (preventative drugs), and screening that can impact their health. Using the platform, the health providers 226 may make shared decisions with the members/patients 132 to help the members/patients 132 live healthier lives over time and through active participation and attendance of the healthy counseling programs 202 and health intervention programs 203 recommended or offered through the administrative entity 136 and application 128. Because the health providers 226 have medical backgrounds and qualifications, there will be a medical relationship between the health provider 226 and the member 132, including doctor-patient relationship.

Initially, a user will be evaluated for eligibility to join the preventative care and health intervention application 128 and to participate in the health intervention programs 203 as further described below. The eligibility may be determined based on a set of applicants provided responses to a set of questions or the applicant's electronic medical records (EHRs) that are aimed at determining whether the applicant has any medical histories, existing conditions, or other health concerns that prevents the applicant from joining. The applicant will also go through a complete Health Evaluation process with the automatic processes and the health providers to determine their eligibility of accessing the Health Intervention Programs. The health providers 226 may override a recommendation of rejection based on an assessment of the fitness of the applicant and other criteria. If the applicant is determined to be eligible, the member 132 may further create their health profile with personal information, family histories, questions about lifestyle, interested topics etc. After developing the health profile, the member/patient 132 can choose a health provider 226 and schedule an online visit. During the online visit, the health provider 226 can evaluate the patient's 132 health profile, assess the health risks, give recommendations, and make shared decisions with the member 132/patient on the next steps of lifestyle change, and recommend health intervention programs that could be beneficial to the member 132. The preventative care and health intervention application 128 can help members 132 track their health endeavors and activities over time. In a non-limiting embodiment, additional services provided by the preventative care and health intervention application 128 (as assisted also through the management of the administrative entity 136 and/or health providers 226) may be to evaluate members 132 overall health risks through their family history, current health condition, occupation, lifestyle, nutrition, daily activities, and health risks. Further services may include providing recommendations regarding lifestyle changes, prescribing necessary genetic testing, lab tests or medical exams as necessary, prescribe preventative drugs such as aspirin, insulin, ACE inhibitors, statins, and SSRIs as necessary and so on, recommend health intervention programs (e.g., health counseling services 202 and health intervention programs 203) that can assist in members 132's lifestyle changes, as well as ongoing check-ins with members 132 to adjust the strategies to keep the members 132 progressing.

The medical tier of the preventative care and health intervention application 128 (or platform) may further relate to the health providers 226 seeing members 132, evaluating their medical status, prescribing medication, referring members to other medical diagnosis or treatment, and reviewing eligibility for further engaging in the one or more health intervention programs 203 offered or coordinated through the preventative care and health intervention application 128 on a regular basis.

As noted above, an important tier or level of the preventative care and health intervention application 128 is to provide counseling and guidance to members 132 regarding specific lifestyle changes that can help improve the members 132's physical, mental, and social health. One of the reasons may be that when members 132 engage and spend more time in healthy activities, the members 132 will feel more ownership of their health and make wiser daily choices to reduce their time engaging in activities that are harmful to their health. Accordingly, an important component of the preventative care and health intervention application 128 is the inclusion of the health intervention programs 203, which may be a network of structurally designed activity programs that engage users/members 132 to exercise, eat healthy, meditate, reduce stress, sleep well, adopt other healthy habits, and live healthy lifestyles and so on. As noted with respect to FIG. 2D, part of evaluation of the healthiness of a member 132 is evaluating and understanding the mental and social health of the member 132. FIG. 2D includes an exemplary table 268 with relevant factors/criteria for evaluation by a health provider 226 and incorporation in the health score system 204 and health value score scale 216, which includes relevant factors/criteria analyzing the health benefits of the Health intervention Programs. In this respect, there is a three measure scale are adopted to measure the physical, mental, and social health benefits of the programs.

Further, in a non-limiting embodiment, data can be tracked and aggregated to obtain an attendance and performance score 217, as shown in FIG. 2A, in order to determine whether the member 132 attends the recommended health intervention programs 203 with regularity and how the member 132 is performing with respect to recommended actions in such health intervention programs 203.

The term "health" as used herein may be a comprehensive definition of health and may reflect on a member's physical and mental health as well as the member's social health or social well-being. One of the aims of the preventative care and health intervention application 128 may be to improve the overall health of the member 132 in not just one area, such as the physical health, but in all of these specific areas (i.e., physical, mental, and social). In this way, the preventative care and health intervention application 128 has multiple benefits and roles to play that fills in the gaps and deficiencies of traditional medical services and lifestyle coaches or lifestyle services. The major three categories of the preventative care and health intervention application 128 may include the three dimensions of health values 218 which are physical, mental, and social health, because humans require all three categories to function and thrive. This cumulative focus on these three aspects of a member 132's health follows the World Health Organization (WHO)'s definition of wellbeing which is "a state of complete physical, mental, and social well-being and not merely the absence of disease or infirmity. Accordingly, the preventative care and health intervention application 128 may focus on the member 132 as a whole and helping the member 132 achieve healthy habits in all these dimensions.

It is noted that as part of the social well-being of the member 132, the preventative care and health intervention application 128 may further provide recommendations for healthy social entertainment and healthy residential living locations/habits in one or more non-limiting embodiments.

One of the objectives of the preventative care and health intervention application 128 is to make it easier for members 132 to stick with consuming healthier products and to focus on healthy activities. There may be a series of programs that fall under health counseling services 202 and health intervention programs 203 to assist with such an objective. The preventative care and health intervention application 128 may collaborate with a network of online and offline service providers to deliver such health counseling services 202 and health intervention programs 203 which may include but are not limited to: 1) heathy grocery shopping programs guided by dieticians and/or nutritionists 2) group exercise/sports programs with or without a coach 3) meditation and yoga 4) coached support groups 5) outdoor activity programs 6) reading groups 7) health education groups 8) quality of sleep groups 9) preventative health education 10) emergency preventative medicine delivery services 11) first aid education and training 12) women/children personal safety education 13) cardiovascular disease prevention 14) sexually transmitted disease prevention and 15) sports injury prevention education and so on.

Any of the health counseling services 202 and health intervention programs 203 offered through the preventative care and health intervention application 128 may be added based on several criteria, which may include, but are not limited to, health value, feasibility, and service quality. The health counseling services 202 and health intervention programs 203 may be assessed regularly for their effectiveness, reviews from members 132, quality of service offered, etc. Further, while providing the health counseling services 202, health providers 226 may be very selective in determining which health intervention programs 203 to recommend or unlock access to for each member 132. As noted above, health providers 226 may be qualified individuals to determine whether a member 132 is eligible to participate in the health intervention programs 203, in particular, at full extent and level or with partial restrictions or full restrictions. The health providers 226 may conduct a Health Evaluation, which takes into consideration the age, medical history, current physical health, mental health, and social health conditions, of the member 132 before determining whether to unlock access to a health intervention program 203.

FIG. 2A includes various components that are part of or connect via a network 142 with the preventative care and health intervention application 128. The health intervention provider 228 as shown in FIG. 2A may be responsible for providing health intervention programs 203 to the members 132 in one or more non-limiting embodiment. The health intervention program designer 230 may be responsible for the design of the health intervention programs 203. The lifestyle program evaluation committee 232, as also shown in FIG. 2A, may be responsible for the approval and assessment of the health intervention programs 203 on the preventative care and health intervention application 128. The health intervention program designers 230 design their health intervention programs 203 to maximize the physical, mental, and social health values. The program designers 230 may design a single dimensional program or be creative in designing the health intervention programs 230 to encompass a combination of multiple health dimensions. For example, the health intervention provider 228 may incorporate a 30-minute aerobic exercise and a 30-minute mediation as part of one session that the member 132 must or is asked to attend by the health provider 226 in order to improve the physical health score 206, mental health score 208, and social health score 210 of the member 132. The program provider 228 can also define the best time of day to provide the program 203 in a non-limiting embodiment. The program provider 228 may also add interactive components to the aerobic exercises that require a companion in order for the members 132 to acquire points for increasing the member 132's social health score 210 by participating in that specific program 203 with one or more companions.

The health intervention programs 203 may be provided as an online video program, indoor activity, outdoor activity, a computer-based application that is accessible from a user computing device 101, an online video program, or even may require travel to a nearby or remote location. The program designers 230 may choose to design the health intervention programs 203 in a myriad of ways to maximize the three health categories of physical health, mental health, and social health of the member 132. The following provides a few non-limiting examples of health intervention programs 203 that may be incorporated and tracked with the preventative care and health intervention application 128. In a non-limiting embodiment, there may be a program 203 in the form of a smartphone application that monitors the member 132's screen use time and rewards the member 132 for limiting the smartphone screen use to under 2 hours per day. There may be another exemplary health intervention program 203 that is an after work outdoor activity program that encourages the member 132 to stretch, exercise, and unwind outdoors with the goal of avoiding vision and carpal tunnel issues that occur after prolonged computer use. Another exemplary program 203 may include a guided fitness trip or encouraging the member 132 to walk to a nearby location to purchase a free lottery ticket (coordinated with the preventative care and health intervention application 128).

The health intervention program designers 230 may submit their program proposal and specific design for review by the lifestyle program evaluation committee 232 whose responsibilities may include evaluating the different member 132's eligibility to use any of the health intervention programs 203, evaluate conditions for participation such as time, frequency, environment, and/or equipment for each eligible member group 132. The responsibilities of the lifestyle program evaluation committee 232 may further include identifying if there are any safety risks for each eligible user group, evaluating the health values 218 of the health intervention programs 203 using the health value score scale 216 (including physical, mental, and social health), and determine the base health score to be earned by each user group if the health intervention program 203 is fully attended and participated in by the members 132. Once the lifestyle program evaluation committee 232 has approved any of the health intervention programs 203, the health intervention program 203 may be listed in preventative care and health intervention application 128 and a health provider 226 may prescribe one or more selected health intervention programs 203 to any particular member 132. In a non-limiting embodiment, the health provider 226 may prescribe a select health intervention program 203 after the health provider 226 has performed a basis Health Risk Assessment (HRA) and risk stratification assessment 212 (i.e., health risk assessment) and developed an initial set of health scores 206, 208, 210 to better understand the needs of the member 132.

The attendance, participation, and completion of the health intervention programs 203 may be tracked by a combination of sources. The preventative care and health intervention application 128 may track the attendance by requiring the member 132 to check in and check out. Further, the application 128 may track the attendance via phone app automatic tracking and other wearable devices/ electronic devices 150 which may include smartphones or smart glasses or various other wearable devices/electronic devices 150. The participation of the members 132 in the health intervention programs 203 may be further tracked by the program provider's 228 evaluation and notes, attendance of online programs 203, attendance of the in-person programs 203, online surveys or quizzes, and other tracking tools and participation tools. As shown in FIG. 2A, there may be an intervention programs record 224 which is a compilation of data reflecting the member 132's participation, attendance, and completion of the one or more health intervention programs 203. The intervention programs record 224 may further include notes, comments, evaluations, and analysis provided by one or more parties with respect to the member 132's participation in a health intervention program 203, and may include such notes from the program provider 228, member 132 (self-evaluation and review), and/or health providers 226.

A third tier or notable aspect of the preventative care and health intervention program 128 is the inclusion of a health score system 204. The health score system 204 is incorporated as an integral component of the preventative care and health intervention application 128. The health score system 204 and health value score scale 216 may be designed to include and/or measure a 1) Health Risk Assessment Score which serves to reflect the accurate health status of the member 2) commitment to the health intervention programs, which reflects members' effort and performance in the health intervention programs and 3) medical treatment the member goes through, which may reflect the health value/ risk of the medical treatment (drugs, surgeries or IVs etc.)

The health score system 204 is utilized to reflect a true health value 218 of the member 132. In a non-limiting embodiment, the health value 218 may fall under at least three major categories which includes the physical, mental, and social well-being of the member 132.

This health score system is developed to reflect a members' change of health status over time based on their health status, commitment to the health intervention programs, and other medical diagnosis and procedures including medication, therapies, and surgeries etc. The health score system is a proactive and dynamic way of measuring member's health change.

The health score system is composed of three major components: health scores from Health Evaluation, from Health intervention Programs, and from other medical diagnosis and procedures. Each component is further composed of three dimensions namely physical, mental and social dimensions. Each component and dimension can be combined with algorithms to reflect their overall health score. And an ultimate health score for each member will be calculated combining all the components and dimensions.

In a non-limiting embodiment, the health evaluation score measures a member's current health conditions and health risks they are exposed to. The Health Evaluation Score is designed to reflect the scientific health status of a member. Factors taken into the Health Evaluation Score include but not limited to Health Questionnaire Result, Health Risk Assessment Result, Family History, Previous and Current Health Conditions, lab test results, and diagnosis reports. Each factor is assigned with its weight, and the provider's opinions are also incorporated in determining the Health Evaluation Score. The Health Evaluation Score is composed of three dimensions: physical, mental and social health. These three dimensions are calculated respectively, and an algorithm is developed to combine these three dimensions to reflect the Overall Health Evaluation Score.

The Performance Score of Health intervention Programs measures a member's compliance, adherence, performance in the Health intervention Programs. The Performance Score of Health intervention Programs is designed to reflect the health benefits (and sometimes health risks) that members acquire by participating in the Health intervention Programs. When the Performance Score of Health intervention Programs is being calculated, these factors are considered: health benefits (and risks) of the Health intervention Programs participated, member's attendance, performance, coach's feedback etc. The same as the Health Evaluation Score, the Performance Score of Health intervention Program is also composed of three dimensions: physical, mental and social health. These three dimensions are calculated respectively, and an algorithm will be developed to combine these three dimensions to reflect the Overall Performance Score of Health intervention Programs.

The Medical Intervention Impact Score measures the health impacts of medical interventions on a member. These medical interventions include but not limited to diagnosis, procedures, medication, therapies, surgeries, and other provider-prescribed medical services. These provider-prescribed medical interventions can bring either positive or negative impacts to members' health status. When evaluating the Medical Intervention Impact Score, several factors are considered including but not limited to: health benefits and risks of the medical intervention to the member, recovery time, impacts on members' participation of Health intervention Programs, and doctor's opinion etc. Similarly, to the other two Health Score types, the Medical Intervention Impact Score is also composed of three dimensions: physical, mental and social health. These three dimensions are calculated respectively, and an algorithm will be developed to combine these three dimensions to reflect the Overall Medical Intervention Impact Score.

The Physical Health Score reflects a member's physical health benefits (or risks) acquired through the Health Evaluation, Performance of Health intervention Program, and Impact from Medical Interventions. The measurements of the physical health scores can be collected from Health Evaluation process (health risk assessment such as family history, existing health status, self-reported habits, living environment etc.; medical exams such as blood pressure, lab tests, medical imaging reports, cancer screening etc.; members' electronic medical records (EHR) telling the medical history of the member). The measurements of the physical health scores can also be collected from the Health intervention Programs such as electronic kiosks and devices used by the member during the Health intervention Program, wearable devices, members' self-reported feedback, physical test results, Program coaches' feedback and so on. Additionally, the physical health can be measured by the Medical Intervention Impact, which is measured by benefits/risks incurred in the medical interventions, recovery time, doctor's opinions on the recovery of the member, and doctor's re-evaluation of the member's health. These three components are calculated respectively, and an algorithm will be developed to combine these three components to reflect the Overall Physical Health Score of the member at any specific times.

The Mental Health Score reflects a member's mental health benefits (or risks) acquired through the Health Evaluation, Performance of Health intervention Program, and Impact from Medical Interventions. The measurements of the mental health scores can be collected from Health Evaluation process (health risk assessment such as family history, existing health status, self-reported habits, connectedness with family and friends, living environment etc.; medical exams such as blood pressure, lab tests, medical imaging reports, cancer screening etc.; members' electronic medical records (EHR)). The measurements of the mental health scores can also be collected from the Health intervention Programs such as electronic kiosks and devices used by the member during the Health intervention Program, wearable devices, members' self-reported feedback, mental test results, Program coaches' feedback and so on. Additionally, the mental health can be measured by the Medical Intervention Impact, which is measured by benefits/risks incurred in the medical interventions, recovery time, doctor's opinions on the recovery of the member, and doctor's re-evaluation of the member's health. These three components are calculated respectively, and an algorithm will be developed to combine these three components to reflect the Overall Mental Health Score of the member at any specific times.

The Social Health Score reflects a member's social health benefits (or risks) acquired through the Health Evaluation, Performance of Health intervention Program, and Impact from Medical Interventions. The measurements of the social health scores can be collected from Health Evaluation process (health risk assessment such as family history, existing health status, self-reported habits, connectedness with family and friends, living environment etc.; medical exams such as blood pressure, lab tests, medical imaging reports, cancer screening etc.; members' electronic medical records (EHR)). The measurements of the social health scores can also be collected from the Health intervention Programs such as electronic kiosks and devices used by the member during the Health intervention Program, wearable devices, members' self-reported feedback, mental test results, Program coaches' feedback and so on. Additionally, the social health can be measured by the Medical Intervention Impact, which is measured by benefits/risks incurred in the medical interventions, recovery time, doctor's opinions on the recovery of the member, and doctor's re-evaluation of the member's health. These three components are calculated respectively, and an algorithm will be developed to combine these three components to reflect the Overall Social Health Score of the member at any specific times.

The Overall Health Score may include Overall Physical Score, Overall Mental Score, Overall Social Score, Overall Health Evaluation Score, Overall Performance Score of Health intervention Programs, Overall Medial Intervention Impact Score, and the Total Overall Score, which is calculated with algorithm combining all the components (Health Evaluation, Health intervention Program Performance, Medical Intervention Impact) and all the dimension scores (physical health, mental health, and social health scores). Considering these components and dimensions are intertwined with each other, algorithms are also developed to measure the association among different components and dimensions. For example, going through a medical intervention can further affect a member's Health Evaluation result and their performance in the Health intervention Programs. All these factors will be considered when calculating the Overall Health Score when a member has gone through medical interventions.

In a non-limiting embodiment, members 132 are provided with an initial set of health scores 206, 208, and 210 that relates to their physical, mental, and social health. The initial set of health scores 206, 208, 210 may originate from a combination of sources as further elaborated upon in FIG. 3 and FIG. 4. For example, in a non-limiting embodiment, the initial set of health scores 206, 208, and 210 may be an aggregation of data related to the personal medical history 210 of the member 132. The personal medical history 210 of the member 132 may include all relevant aspects of the member 132's physical and emotional and mental health history. Further, the preventative care and health intervention application 128 includes data structures and data bases that may be accessible from the data storage systems 140 from the hosting system 138 that include prediction engines that may incorporate relevant existing data about various medical conditions, illnesses, issues that become present to people having certain factors. Such factors, may include, but are not limited to, age, gender, weight, height, BMI, blood pressure, cholesterol levels, any chronic disease issues related to kidney, lungs, smoking history, alcohol use, and/or drug use. These factors and others may be utilized by the prediction engines to help calculate and provide an initial set of physical health scores 206, mental health scores 208, and social health scores 210. These initial set of scores 206, 208, and 210 are not static and may be changed and altered for various reasons. The health provider 226 assigned to the member 132 may further adjust and edit the initial set of physical health score 206, mental health score 208, and social health score 210. Further, as the member 132 participates in the health counseling services 202 and health intervention programs 203, after a period of time, a re-evaluation will be performed to determine if the physical health scores 206, mental health scores 208, and social health scores 210 can be updated and reflect any change or not, including an improvement. Further, the score system may include health scores from Health Evaluation, from Health intervention Programs, and from other medical diagnosis and procedures. Each component is further composed of three dimensions namely physical, mental and social dimensions.

One of the aims of the health score systems 204 is to reward members 132's adherence to the health counseling services 202 and health intervention programs 203 for multiple reasons. In this manner, there should be a steady improvement in the overall health of the member 132, including the physical, mental, and social health of the member 132. Further, the member 132 may take advantage of rewards offered through the preventative care and health intervention application 128. Additionally, the health provider 226 or other individual may evaluate the member 132's feedback and responsiveness to the selected programs from among an initial set of health counseling services 202 and health intervention programs 203 and then assess and recommend additional health counseling programs 202 and health intervention programs 203 that the member 132 may further benefit from.

The health score system 204 may help to reward members 132 for their adherence and performance, and may include a performance score to rate the quality of performance of the member in the one or more health intervention programs. The health score system 204 is an objective means for assessing the health of the member 132. One of the notable features of the preventative care and health intervention application 128 is that members 132 can earn or accumulated updated and improved health scores 206, 208, 210 with the goal of achieving a maximum, potential level. Participating in the health counseling services 202 and, in the health, intervention programs 203 allows the members 132 to accumulate and earn updated health scores 206, 208, 210. It is important that the members 132 participate in and adhere to regular activities and requirements associated with the health intervention programs 203 in order to improve their initial set of physical, mental, and social health scores 206, 208, and 210. Accordingly, the health value score scale 216 follows these three dimensions of focus on physical, mental (including emotional), and social well-being and health and a user/member 132 has a base initial set of health scores 206, 208, 210 when the user 132 if first enrolled and evaluated, but can show improvement with time and adherence to the health intervention programs 203 and earn updates to the scores 206, 208, 210. A combo health score 214 as shown in FIG. 2A may be a unique type of health score in which the member 132 can combine a program for physical and mental health. Upon completion of such a program, the member 132 may earn combo health scores 214 showing diversity and consistent participation over time.

As noted above, the member 132 can earn physical, mental, and social health scores 206, 208, 210 integrated as part of the health score system 204 of the preventative care and health intervention application 128. In a non-limiting embodiment, each health value 218 is 1 point in the health value score scale 216. Each member 132 may earn, in a non-limiting example, up to 100 points for each dimension on a weekly basis, i.e., 100 points for physical, mental, and social health scores, respectively, totaling 300 points. For example, if the health intervention programs 203 has incorporated a 30-minute aerobic exercise and 30-minute meditation that encourage the member 132 to have a companion in the program 203, and a member has completed the one-hour session on his or her own, the member 132 may gain a health value score/point 218 in both the physical and mental categories. If the member 132 has invited a friend/family member to join the member 132, the member may also earn a health value score/point 218 in the social category. If the member 132 has only completed the 30-minute aerobic exercise and then drops the program 203, the member 132 may still earn the health value scores 218 for the aerobic exercise.

In a non-limiting embodiment, there may be program coaches that assist in monitoring and evaluating members 132 attendance, participation, and completion of the health counseling services 202 and/or health intervention programs 203. The program coach can evaluate the participation of the members 132 during one or more programs 202, 203 on a 0-100% scale. If the member 132 has shown up and completed the required preventative care health counseling, and health intervention related activities, the member 132 will receive a 100% health value score 218 for that particular program 202 or 203. On the other hand, if the member 132 has merely shown up but did not really commit or perform any of the required activities or follow up exercises, the program coach may determine that the member 132 has not earned the full health value score 218 or any of the health value score 218. Considering that the health intervention programs 203 may comprise different activities that can contribute to the physical, mental, and social wellbeing of the member 132, the program coach can evaluate these three categories respectively.

The combo health scores 214 are developed to encourage users to complete the recommended health intervention programs 203 with consistency and diversity in participating in the health intervention programs 203 and commitment to the programs 203 over a reasonable period of time. For example, purposes only, if a user/member 132 has participated in 80% of the programs 202, 203 recommended by a health provider 226 on a weekly basis, the member 132 may earn an extra 20% in health value scores 218 in a non-limiting example. In order to encouraging diversity in attendance and participation with the health intervention programs 203, the preventative care and health intervention application 128 may reward users 132 who have shown diversity in their participation, with the physical, mental, and social health scores 206, 208, 210 showing a level or increase to a certain minimum threshold. The application 128 may unlock or provide rewards and incentives to the member 132 in the form of points redeemable for money, including cash or credit, cryptocurrencies, in kind purchases, experiences, services, or any other type of reward/incentive.

It is further encouraged for the member 132 to show consistency with respect to the health intervention programs 203. Accordingly, a certain percentage of the health values score scale 216 may evaluate the consistency of the member 132 in attending the various selected health intervention programs 203. The health scores 206, 208, 210 can show a decrease if the member 132 stops participating in the health intervention programs 203 each week or based on another metric or minimum threshold of participation/attendance. This may result in lowering one or more of the physical, mental, or social scores 206, 208, 210 for the health score system 204 and may result in the health provider 226 and/or program provider 228 reaching out to the member 132.

One or more electronic devices 150 may be used to help determine the physical health score 206, mental health score 208, and social health score 210. Additionally, genetic testing, lab tests, medical consultations, and questionnaires may also be used to determine the physical health score 206, mental health score 208, and social score 210. Accordingly, the preventative care and health intervention program application 128 may include databases that can collect any data provided by the electronic devices 150 relevant to the member 132's physical, mental, and/or social health. Such data will be sorted and weighted to determine the physical health score 206, mental health score 208, and social health score 210. Such electronic devices 150 may include sensors/electrodes/electronic devices for obtaining data/detecting the member 132's glucose levels, blood pressure heart rate, electroencephalogram (EEG) sensors/tests to detect electrical activity in the brain, temperature, airflow and oxygen levels, weight, BMI, and any other factor.

Returning to FIG. 1C, in a non-limiting embodiment, FIG. 1C shows one or more unique aspects of the preventative care and health intervention application 128. In a non-limiting embodiment, as noted above, the health providers 226 have their own electronic devices 150a enabling them to accomplish a number of functions and activities with respect to their role for the preventative care and health intervention application 128. In a non-limiting embodiment, the medical and/or health providers 226 may initiate video interviews with members 132 and view personal data and information through the preventative care and health intervention application 128. This may include viewing health history, imaging lab and diagnostic results, any relevant questionnaires, participation records if the health intervention programs 203, health scores from the health scoring system, and anything relevant to the health of the member 132.

The health providers 226 may also set health goals for the members 132 that are visible to the member 132 and/or health intervention providers 202 or other parties via various interfaces of the preventative care and health intervention application 128. Further, the medical providers 226 may use their electronic devices 150a and access to the preventative care and health intervention application 128 to revies a member's 132 participation record, adjust goals for the member 132, develop questionnaires for the member 132 to fill, and/or edit the health records for the member 132. Further, the medical providers 226 via their electronic devices 150a may prescribe health intervention programs 203 that the member 132 may participate in, including providing approval or disapproval for particular health intervention programs 203. The medical providers 226 may also set up the mode, intensity, frequency, start date, and end date for any approved health intervention programs 203. Further, the medical providers 226 may assign weight to the health scores 204 of the health intervention programs 203. Further, the medical providers 226 may view the profiles of the health intervention programs 203 in the network and any targeted populations. Further, the medical/health providers 226 may also prescribe pharmaceutical drugs/medicines, personal medical devices, labs, physical therapies, or other medical services that the members 132 need. Further, the medical providers 226 may schedule return visits with the members 132.

For the electronic devices 150b associated with the health intervention providers (HIP), there may be a number of functions and activities that may be performed using the preventative care and health intervention application 128 on the member's 132 behalf. For example, any of the electronic devices 150b of the HIP providers may be utilized to check in members 132 and verify the identity of the members 132 using any methods including, but not limited to phone numbers, fingerprints, face recognition, or other biometric technologies. Further, the electronic devices 150b may be used to pull a prescription list for a member 132 as provided by a current health intervention program, as well as to verify a member 132's eligibility to participate in the health intervention programs 203. Further, the electronic devices 150b may be used to verify the mode, intensity, frequency, start date, and end date of the health intervention programs 203 as determined by the health/medical provider 226. Further, the electronic devices 150b may be used to approve a member's participation in a health intervention program 203, and to collect various data related to a member's participation in one or more health intervention programs 203.

Various sensors may be used and assigned to the member 132 in order to track a member's participation, location, heart rate, blood pressure, and any other metric that may be measured using sensors. The data from the sensors may be fed through the preventative care and health intervention application and stored for use by a machine learning engine 193 in one or more non-limiting embodiments. Such data and feedback from the sensors may be used for the clinical decision module 195, the health intervention program benefit evaluation module 196, or the patient health scoring module shown in FIG. 1C.

As noted above, any health intervention program sensors included in one or more electronic devices 150 and/or otherwise connected to a member 132 can be used to measure physical actions, motions, movements and/or which body muscles are engaged by a member 132. Further, the sensors may be used to measure any weight used in the program, food and/or nutrition consumed, engagement level of conversations, intensity, frequency, duration of the activities, and any other relevant health measures that reflect a member's mental, physical, and social participation in the one or more health intervention programs 203. Any such data may be transmitted to the preventative care and health intervention application 128 via the one or more electronic devices (e.g., 150a, 150b, or 150c).

In a non-limiting embodiment, the electronic devices 150c of the member 132 is a personal apparatus or personal health device that may be a smart device. The electronic device 150c may be used to access one or more interfaces of the preventative care and health intervention application 128 and utilized for a number of functions, including scheduling and seeing medical providers 226 using online video resources, viewing personal data and medical history and information included in the preventative care and health intervention application 128, update any such data, view prescriptions from medical providers 226 for medicine and/or health intervention programs 203, order medicine and/or other medical devices, and schedule appointments. Further, the member 132 may utilize any features of the electronic device 150c for biometric identification and verification to authenticate the member 132 including through face, finger, sound, iris, or any other biometric identification method. Further, using wearable devices and other sensors, the electronic device 150c may collect relevant data about the member 132. Any data from the electronic device 150c and other wearable devices and/or sensors may be uploaded to the profile of the member 132 in the preventative care and health intervention application 128.

In a non-limiting embodiment, FIGS. 2B, 2C, and 2D are tables that may display various factors and considerations integrated into the health score scale 216 and health score system 204. FIG. 2B shows a physical health table 260 that may show the body systems as categorized by the ICD-10-1 codes from the World Health Organization. FIG. 2C shows a mental health table 266 and FIG. 2D shows a social wellbeing table 264. The tables 260, 266, 264 shown in FIGS. 2B-2D may include various systems 262 assigned health points 264 and may be integrated into the engines and systems that are part of the preventative care and health intervention application 128 to generate the physical health scores 206, mental health score 208, social health score 210 and utilized in the health value score scale 216. In real environment, the system may adopt other standard categorization system as reference for these score scales.

The relevant data systems 262 shown in a non-limiting example for evaluating a physical health of a member 132 may include, but are not limited to, testing and evaluating the central nervous system, peripheral nervous system, heart and great vessels, upper arteries, lower arteries, upper veins, lower veins, lymphatic and hemic system, eye, ear, nose, sinus, respiratory system, mouth and throat, gastrointestinal system, hepatobiliary system and pancreas, endocrine system, skin and breast, subcutaneous tissue and fascia, muscles, tendons, bursae and ligaments, head and facial bones, upper bones, lower bones, upper joints, lower joints, urinary system, female reproductive system, male reproductive system, general anatomic region, and more specifically the upper extremities anatomical region, and lower extremities anatomical region, as shown in the physical systems table 260 in FIG. 2B.

The relevant data systems 262 shown in a non-limiting example for evaluating a mental health or psychological well-being of a member 132 may include, but are not limited to, testing and evaluating the life purpose, mastery, positive affect, optimism, personal growth, autonomy, sense of coherence, emotional vitality, stress reduction, intellectual capabilities, spiritual wellness, life satisfaction, and cognitive capabilities of the member 132, as shown in the mental health and psychological well-being systems table 266 in FIG. 2C. Further, the mental and emotional health of the member 132 will require evaluation for any psychiatric conditions or disorders related to depression, bipolar syndrome, schizophrenia, anxiety, or any other psychological disorder/condition. A health provider 226 qualified to evaluate such conditions may be paramount in providing recommendations and analysis in this field.

With respect to the social well-being table 268 shown in FIG. 2D, some relevant systems 262 for data integration may include evaluating and determining a level of connectedness with the family, connectedness with friends, connectedness with culture, self-acceptance, helpfulness to others, engagement of group activities, engagement in meaningful conversations, and acquirement of life values for the member 132. These systems 262 as shown in these tables 260, 266, and 268 in FIGS. 2B-2D may be quantified and utilized to enhance the performance of preventative care and health intervention application 128 to automatically evaluate and provide an initial or base set of physical health scores 206, mental health scores 208, and social health score 210 utilized by the health score system 204 to evaluate the health scores of the member 132.

Further, providing a thorough examination and testing of the member 132's physical, mental, and social health by referring to these exemplary systems 262 as shown in FIG. 2B for the physical wellbeing of the member 132 in physical table 260, the mental wellbeing table 266 as shown in FIG. 2C and the social well-being table 268 as shown in FIG. 2D may further be relevant to assist the health provider 226 in providing a risk stratification assessment 212 of the member 132. In a non-limiting embodiment, the health provider 226 may perform a risk stratification assessment 212, which is an assessment and prediction/projection of the possible health risks as they relate to the physical health, mental/emotional health, and social health of the member 132. "Risk stratification" as understood by medical/health providers 226 usually relates to a process of assigning all members/patients 132 a particular risk status based on data reflecting vital health indicators, lifestyle and medical history of the member 132. The systems 262 and relevant exemplary points 264 shown in tables 260, 266, and 268 in FIGS. 2B-2D may be utilized as objective data for the health provider 226 to provide such a risk stratification assessment 212 in a non-limiting embodiment.

Figure 3:
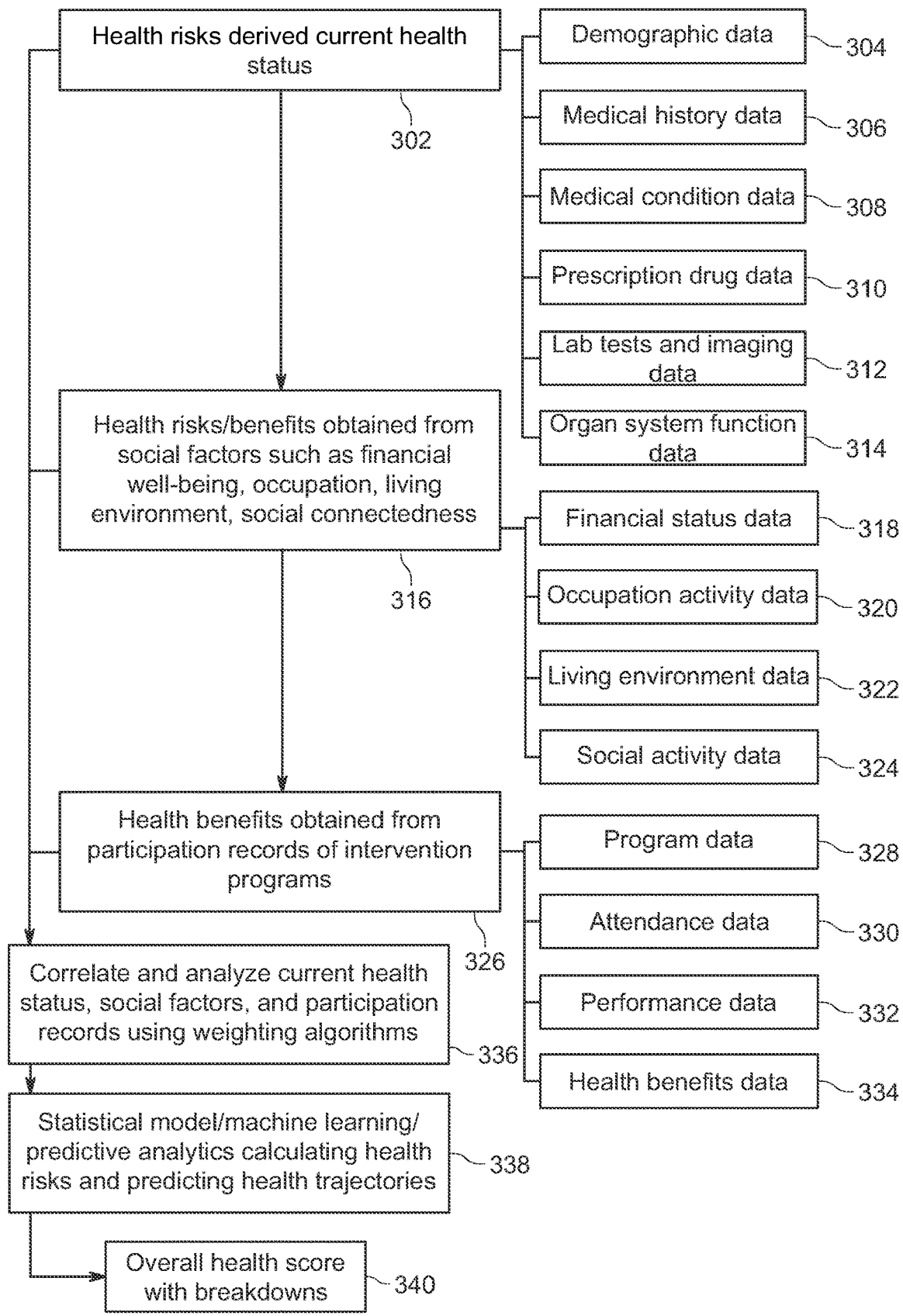
FIG. 3 depicts an exemplary flowchart of a method for assembling criteria for a health score system integrated with the preventative care and health intervention application.

FIG. 3 shows an exemplary flowchart for factors that may be utilized in an exemplary health score system 204. At step 302, the preventative care and health intervention application 128, as shown in FIG. 1 and FIG. 2A, may assess the health risks derived from a current health status/condition of the member 132. This assessment may be in conjunction with or the same as the risk stratification assessment 212 shown in FIG. 2A in one or more non-limiting embodiments. The step 302 to assess the health risks derived from current health status 302 may include analysis and review of demographic data 304 associated with a member 132, medical history data 306, medical condition data 308, prescription drug data 310, genetic testing, lab tests and imaging data 312, and organ system function data 314. At step 316, there may be an assessment of the health risks/benefits obtained from review of various social factors, which may include financial wellbeing of the member 132, occupation, living environment, and social connectedness of the member 132. The data and criteria that may be included in such an assessment of the health risks/benefits obtained from review of various social factors may include, but are not limited to, the financial status data 318, occupation activity data 320, living environment data 322, and social activity data 324 provided by the member 132. Such data and criteria may be further categorized, quantified, and described in one or more social factors evaluation 222 as shown in FIG. 2A, which may further include notes, comments, and evaluations by a health provider 226 or another qualified party regarding the member 132's social well-being.

At step 326, as shown in FIG. 3, there may be an assessment of the health benefits obtained from participation records of the intervention programs records 224. These intervention programs record 224 may include information about the program data 328, attendance data 330, performance data 332, and health benefits data 334 with respect to the member 132's attendance, performance, and participation in the one or more health intervention programs 203.

At step 336, the systems of the preventative care and health intervention application 128 may correlate and analyze current health status, social factors, and participation records using weighting algorithms and other systems. At step 338, the using various predictive analytical engines, statistical models, and machine learning, the preventative care and health intervention application 128 may calculate the health risks and predict health trajectories. This calculation of the health risks and prediction of health trajectories may be incorporated in the risk stratification assessment 212 as discussed above and shown in FIG. 2A in one or more non-limiting embodiments. At step 340, the overall health score with breakdowns into individual physical health scores 206, mental health score 208, and social health scores 210 may be provided to the member 132 via the preventative care and health intervention application 128.

Figure 4:
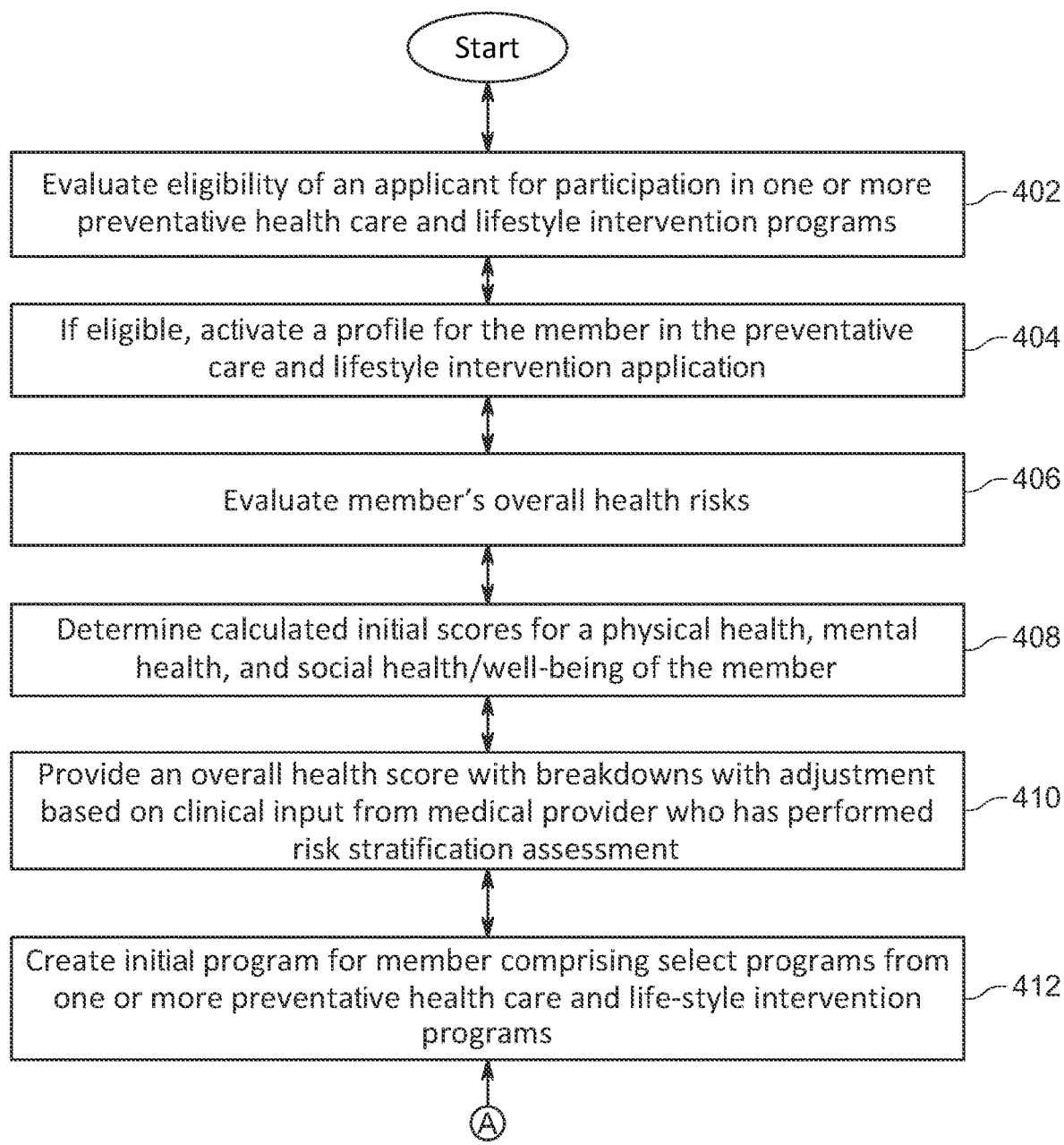
FIG. 4 depicts an exemplary flowchart for using a preventative care and health intervention application.
Figure 4:
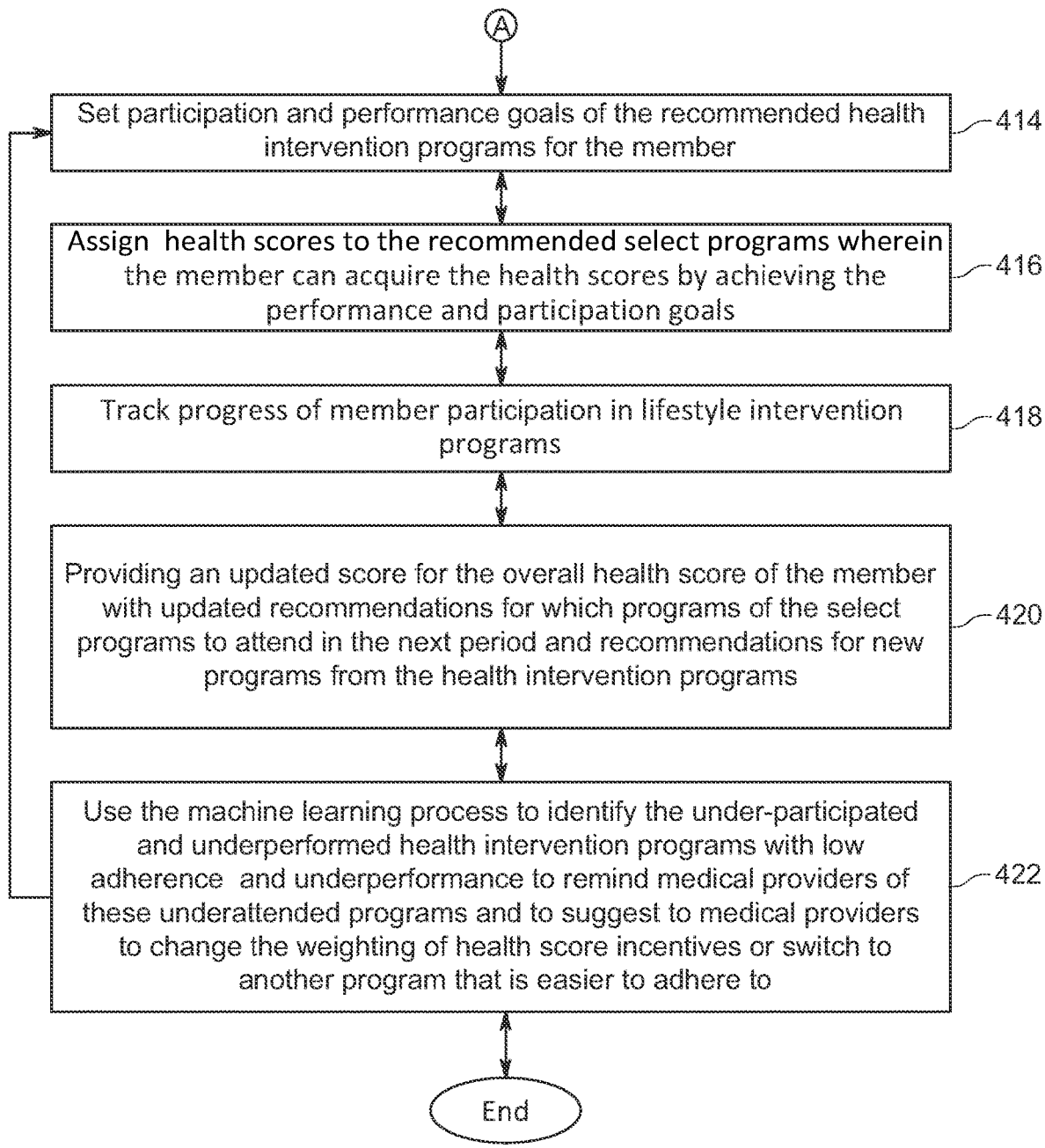

FIG. 4 provides another exemplary flowchart with more detailed steps for one or more aspects of the preventative care and health intervention application 218. As shown in FIG. 4, at step 402, the exemplary method may include evaluating the eligibility of an applicant for participation in one or more preventative health care and health intervention programs 128. This step may further comprise screening an applicant for eligibility to participate in the preventative care and health intervention application 128 by using a set of questions and applicant provided responses to the set of questions. The screening may include automatically analyzing the applicant provided responses to the set of questions about the medical health and background of the applicant with the goal of detecting if a medical condition or some other type of condition is present that excludes participation of the applicant in the one or more preventative care and health intervention programs 203 based on predetermined criteria for excluding an individual. Responsive to detecting the presence of the medical condition or some other condition that excludes participation in the programs 203, the method may include rejecting the applicant for participation in the one or more preventative health care and health intervention programs. It is noted that the health/medical provider 226 can override the rejection of the applicant upon consideration of a total review of the applicant and entire medical history of the applicant. The health/medical provider 226 can provide an assessment of the level of fitness of the applicant for the participation in the one or more preventative health care and health intervention programs 203 and may determine that if the application 128 initially rejects the applicant, that this recommendation is overridden.

At step 404, the method may proceed with activating a profile for the member 132 in the preventative care and health intervention application 128 if the applicant is eligible. This step may further include converting the applicant to being an active member 132 of the preventative care and health intervention application 128. Further, the step may include gathering a member 132's demographic and geographic data and medical history of the member 132. This step may include obtaining the current and historical medical data associated with the member 132, whereby the medical history covers the physical, mental, and social health history. This step may further include assigning one or more health providers 226 assigned to the member 132.

At step 406, the method may include evaluating a member 132's overall health risks. This step may further include evaluating the member 132's overall health risks based on several factors that include, but are not limited to, the member medical history, family history, occupation, lifestyle, nutrition, daily activities, and health risks and the system may utilize one or more questionnaires to obtain this information.

At step 408, the method may include determining and receiving a calculated set of initial set of scores for a physical health 204, mental health 208, and social health/well-being 210 of the member 132. This step may further includes assigning points to the applicant/member provided responses to the set of questions based on a predetermined template and uniform scoring system and totaling the points together for the member provided response.

At step 410, the method may include providing an overall health score with breakdowns with adjustments based on the clinical input from medical provider 226 who has performed risk stratification assessment 212. This step may further include providing an initial physical health score, an initial mental and/or emotional health score, and a third social health score (e.g., scores 206-210). The calculated initial scores for the physical, mental, and social health of the member may be further adjusted based on the clinical institution and input from a medical provider 226 who has performed risk stratification of the member's physical and mental health. Further, the health provider 226 or another party has performed a current assessment of the member 226 and the current lifestyle status of the member 226.

The method may further include prescribing an initial set of programs 202, 203 for a member 132 to participate in comprising select programs from one or more preventative health care and health intervention programs 202 and 203 with the goal to improve the initially calculated and provided health scores. This is shown at step 412, in which the method may include creating an initial program for the member 132 comprising recommendations for select programs from the health intervention programs 203. At step 414, the method may include the medical providers/health providers 226 setting participation and performance goals for the recommended health intervention programs 203 for the member 132. At step 416, the method may include assigning health scores to the recommended select programs 203 wherein the member 132 can acquire the health scores by achieving the performance and participation goals as set by the medical providers 226 in step 414. At step 418, the method may include tracking the progress of the member's 132 participation in the lifestyle and/or health intervention programs 203. At step 420, the method may include providing an updated for the overall health score 204 with breakdowns for the physical health score 206, mental health score 208, and social health score 210 with updated recommendations for which health intervention programs 203 of the selected programs 203 to attend in the next period and recommendations for new programs 203. It is noted that the attendance and performance score 217 shown in FIG. 2A may be calculated at this step 416 in a non-limiting embodiment and utilized in one or more machine learning processes by the machine learning engine 193. The attendance and performance score 217 may also be utilized by the machine learning engine 193 to determine one or more variables for the health intervention program benefit evaluation module 196 and the patient/member health scoring module 197.

At step 422, the method may include using the machine learning process including using the machine learning engine 193 to identify the under-participated and underperformed health intervention programs with low adherence and underperformance to remind the medical providers 226 of these underattended programs 203 and to suggest to the medical providers 226 to change the weighting of the health score 204 incentives or switch to another program 203 that is easier to adhere to. In this sense, the scoring system can achieve multiple objectives including encouraging the member 132 to attend the health intervention programs 203 to achieve positive or high attendance and performance scores 217 in order to benefit from the content and educational information presented by such health intervention programs 203. Further, the medical providers 226 are uniquely provided with necessary data and the ability to track the member 132's attendance of such health intervention programs 203.

Figure 5:
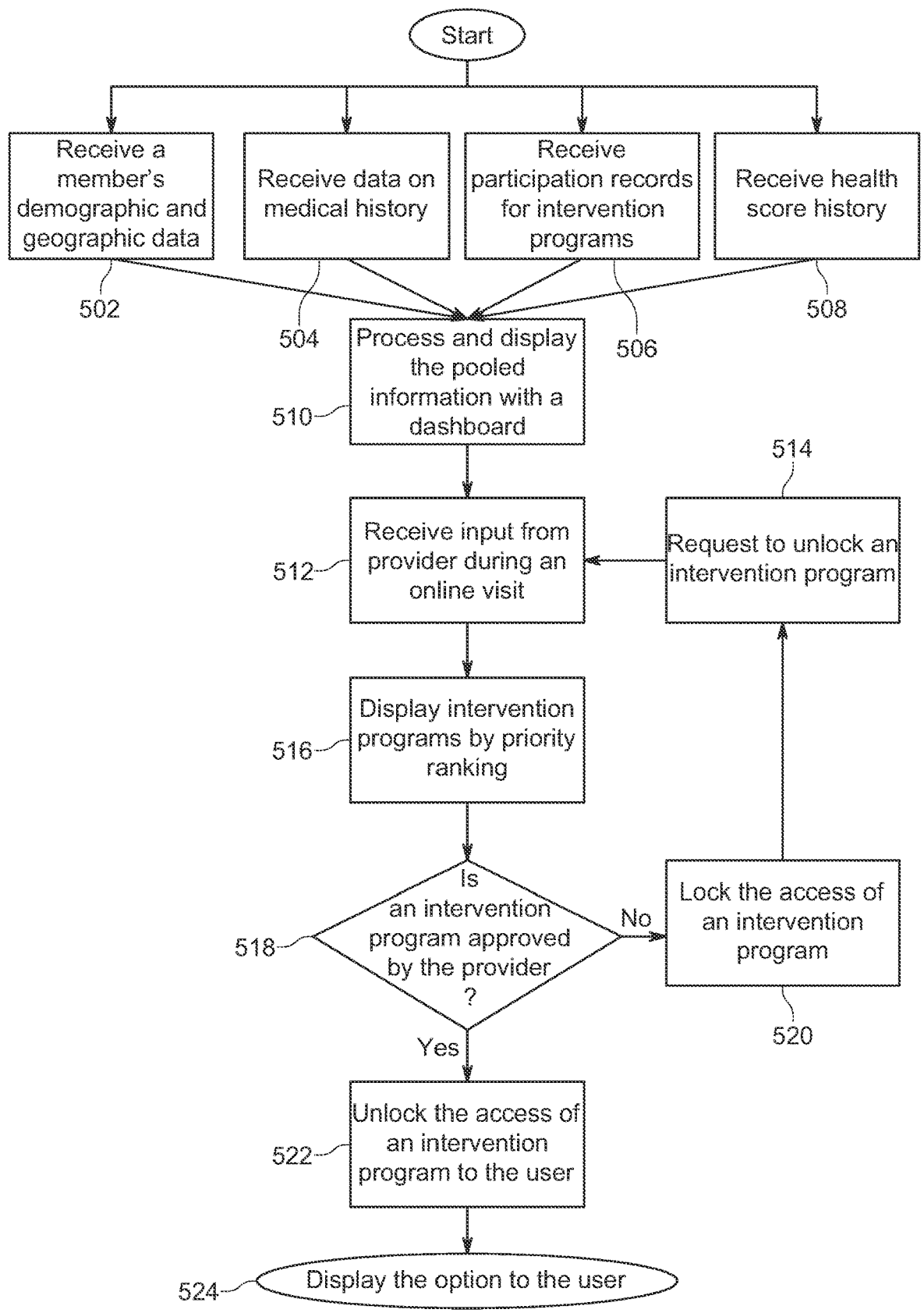
FIG. 5 depicts an exemplary flowchart for a medical provider to make a decision regarding unlocking access to health intervention programs based on a certain set of criteria.

FIG. 5 provides an exemplary flowchart for a health provider 226 and for the preventative care and health intervention application 128 to utilize in the decision making process of which health counseling services 202 and health intervention programs 203 to prescribe and/or unlock access to for the member 132 to participate in after the member 132 has participated in a few programs 202 and 203 after a period of time and has been provided with an initial set of health scores related to the physical health score 206, mental health score 208, and social health score 210. To begin, the method may begin with receiving a member's demographic and geographic data 502, receiving data on the member 132's medical history 504, participating records for intervention programs 506, and receiving a health score history 508. At step 510, the method may include processing displaying the polled information with a dashboard in one or more non-limiting embodiments. At step 512, the method may include receiving input from a health provider 226 during an online visit. At step 514, the method may include requesting to unlock a health intervention program 203. At step 516, the method may include displaying the health intervention programs 203 available by ranking. At step 518, the method may include querying whether there is an intervention program 203 approved by the health provider 226. If not, then the method may include locking access to the health intervention program as shown at step 520. If yes, then the method may include unlocking the access to the health intervention program 203 for the member 132 and displaying as an option to the member as shown at steps 522 and 524.

Figure 6:
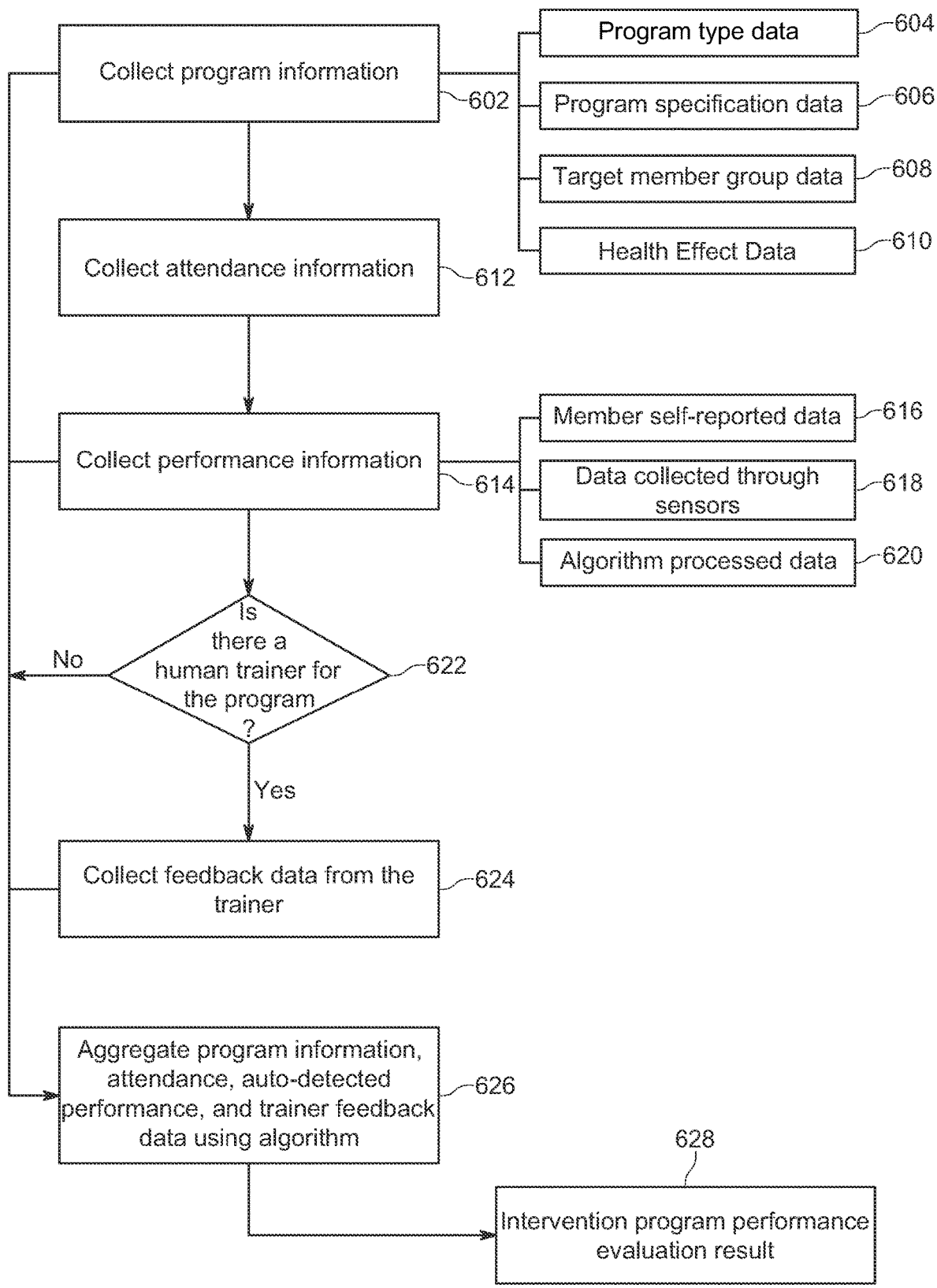
FIG. 6 depicts an exemplary flowchart for evaluations of health intervention programs.

FIG. 6 provides a flowchart for an exemplary method of evaluating a member 132's participation and success with one or more health intervention programs 203. At step 602, the method may include collecting program information, which may further include collecting program type data 604, collecting program specification data 606, collecting target member group data 608, and health effect data 610. At step 614, the method may further include collecting performance information, which may further include colleting member self-reported data 616, data collected through sensors 618, and any algorithm processed data 620. At step 622, the method may include querying whether there is a human trainer for the health intervention program 203. If yes, then the method may include collecting feedback data from the human trainer as shown at step 624. If there is a human trainer who may provide feedback, the method may include aggregating program information, attendance, and auto-detected performance, and trainer feedback data using the algorithm and systems of the preventative care and health intervention application 128 as shown at step 626. Further, even without a human trainer, the method may proceed to step 626 to aggregate program information, attendance, and auto-detected performance, using the algorithm and systems of the preventative care and health intervention application 128.

FIG. 7 provides a flowchart for an example process associated with the clinical decision module 195 shown in FIG. 1C. In a non-limiting embodiment, data obtained via the preventative care and health intervention application 128 may be utilized by the machine learning engine 193 to assist the medical providers 226 in their clinical decision process as to which health intervention programs 203 to approve or disapprove for a member 132 or to recommend the member 132 continues with or discontinues.

As shown in FIG. 7, at step 702, the process includes pulling together or assembling patient's health intervention program attendance and performance data, characteristic data, health data, health score data, and any applicable data from the database 198. At step 704, the method may further include selecting two or more variables of interest from the pulled datasets noted above in step 702. At step 706, the process may include calculating a covariance and any other variables of interest. Such variables that may be calculated include, but are not limited to, Pearson's correlation coefficient, Spearman's correlation coefficient, Kendall rank correlation, Point-Biserial correlation, multiple correlation coefficient, linear regression coefficient, logistics regression coefficient, and/or any applicable coefficients that can represent the associations among the selected two or more variables of interest. At step 708, the process includes generating one or more correlation matrices showing the correlation coefficients between patient's health intervention attendance and performance data and patient's characteristic data, health data, health score data, and any applicable data. In a non-limiting embodiment, the matrices that are presented may be presented as a way to display the correlation coefficients. It is noted that the matrices may be omitted in one or more non-limiting embodiments. Rather, the correlation coefficients may be displayed in one or more lists and the machine learning engine 193 may access the correlation coefficients in order to proceed with steps 708-718 whether the correlation coefficients are displayed as a list or in the form of the matrices.

At step 710, the process may continue with selecting the outstanding correlation coefficients that represent a positive correlation between health intervention attendance and performance data and patient's health data, characteristic data, and performance data and any applicable data variables in the database 198. At step 712, the process may further include returning a list of recommended health intervention programs 203 for the preventative health providers 226 to recommend from a list including a prescription list.

At step 714, the process may include selecting an outstanding correlation coefficient that represents a negative correlation between health intervention attendance and performance data and patient's health data, characteristic data, health data and any applicable data variables in the database 198. At step 716, the process includes returning a list of inadvisable health intervention programs 203 to remind preventive health providers 226 to not select the inadvisable programs 203 from the prescription list for a particular member 132. At step 718, the process 702-716 may be repeated for any data and variables of interested in the dataset.

FIG. 8 is a flowchart for an exemplary process for identifying any potential health effects of a health intervention program 203 on a member 132 or a group of members 132 in order to suggest any potential changes in a program design to the health intervention program providers 228.

At step 802, the process may begin with pulling together or assembling health intervention program attendance and performance data, characteristic data, health data, health score data, and any applicable data from the database 198 for a member 132 and/or a member's representative group. At step 804, the method may include selecting two or more variables from the pulled datasets that can represent patient's characteristics, patient group's participation level of a health intervention program, and the change of health risks of particular diseases from diagnostic data. At step 806, the process may include calculating the covariance and any applicable coefficients (e.g., such as those listed above for step 706 shown in FIG. 7) that can represent the associations among the member 132 group's participation level in a health intervention program 203 and the change of health risks of particular diseases from diagnostic data. At step 808, the process may include generating one or more correlation matrices showing the correlation coefficients between member 132 group's health intervention attendance and performance data and patient's characteristic data, health data, health score data, and any applicable data. In a non-limiting embodiment, correlation matrices may be omitted and rather a list of correlation coefficients is provided and made available for use to the machine learning engine 193 or another component of the preventative care and health intervention application 128 for use in completing steps 810-816.

At step 810, the process may include selecting the outstanding correlation coefficients that represent a positive correlation between a member 132's group attendance and performance in a health intervention program 203 and the member 132 group's change of health risks of particular diseases from diagnostic data. At step 812, the method may include returning the names of health intervention programs (and programs containing certain active doses) that can help members 132 with specific characteristics to reduce the health risks of specific diseases. At step 814, selecting the outstanding correlation coefficients that represent no positive correlation between a member's 132 group attendance and performance in a health intervention program 203 and the member's 132 group change of health risks of specific diseases. At step 816, the method may include repeating steps 802-814 for all applicable data and any variables of interest in the dataset 198. Similar to the process shown in FIG. 7, the steps 802-816 may be implemented by a machine learning engine 193 using one or more machine learning datasets 194 to provide the health intervention program benefit evaluation module 196.

FIG. 9 is a flowchart for a process that may be used to evaluate member scoring with respect to any of the scores (e.g., physical health score 206, mental health score 208, social health score 210, and the overall health score 204 shown in FIG. 2) using a patient/member health scoring module 197 and also utilize a machine learning engine 193 as shown in FIG. 1C.

In a non-limiting embodiment, the process may include Pull together a patient's prescription data and attendance data of health intervention programs as shown at step 902. At step 904, the process may include calculating the attendance rate of each health intervention program 203 based on the prescription data and attendance data. At step 906, the process may include identifying the health intervention programs 203 with lower attendance rates than the average attendance rate of the patient's population group. At step 908, the process may include returning the names of health intervention programs that are under-attended by the patient. At step 910, the process may include increasing the health score weighting by a predefined value assigned to the health intervention programs 203 that are underattended by the member in the medical provider's 226 next cycle of prescribed programs. At step 912, the process may further include returning the recommended health score to medical providers 226 when they are prescribing health intervention programs 203 in any upcoming visits/appointments with the member 132. In a non-limiting embodiment, the weighting provided for the scoring module 197 shown in FIG. 1C may be used to incentive a member 132 to attend certain health intervention programs 203. In a non-limiting embodiment, a goal of the health scoring module 197 is not to reflect the actual health status of a member 132, but to incentivize the member 132 to change the member 132's behavior and adhere to the programs 203 that the medical health providers 226 believe the member 132 will benefit the most from.

Another option for health care providers 226 is to switch members 132 to programs 203 that are easier to adhere to. In this case, the health scoring module 197 can also recommend to add extra points to new physical or other type of activity programs 203 because the members 132 adherence pattern is low for such similar physical or other type of activity programs 203.

Many benefits and advantages are provided by the preventative care and health intervention application 128 as described above in one or more non-limiting embodiment. As noted, before, the traditional health care system is not designed to provide in depth preventative care and to help track and encourage health intervention and improvement in the major three categories related to a member's well-being, which relate to the member's physical, mental/emotional, and social health. The preventative care and health intervention application 128 can be utilized by health providers 226 to see an overall improvement in a member 132's health in all three categories. The preventative care and health intervention application 128 may utilize a unique health scoring system based on a combination of factors, including statistical models and predictive engines and risk stratification sources to provide an accurate and thorough assessment of a member's 132 health in all three categories. Further, the member 132 may be incentivized and rewarded for their participation, attendance, and completion of the one or more health counseling services 202 and health intervention programs 203 to further encourage the member 132's improvement.

Accordingly, the implementations of the preventative care and health intervention application 128, as described in one or more non-limiting embodiments above are numerous. The application 128 may help doctors decide what health intervention program should they "unlock' for a user, track patients participation records and generate activity reports, as well as provide a health Score System to motivate patients and measure the health benefits they acquired through the preventive counseling, health intervention programs, and external medical intervention they go through from physical, mental, and social health dimensions.

Additional advantages and benefits are foreseeable to one of ordinary skill in the art and are within the scope of the invention.

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with; and/or in the context of other particular aspects and embodiments of the invention; and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

"Exemplary" is used herein to mean "serving as an example, instance, or illustration." Any aspect described in this document as "exemplary" is not necessarily to be construed as preferred or advantageous over other aspects.

Throughout the drawings, like reference characters are used to designate like elements. As used herein, the term "coupled" or "coupling" may indicate a connection. The connection may be a direct or an indirect connection between one or more items. Further, the term "set" as used herein may denote one or more of any items, so a "set of items" may indicate the presence of only one item or may indicate more items. Thus, the term "set" may be equivalent to "one or more" as used herein.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or table of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

Specific details are given in the description to provide a thorough understanding of the embodiments. However, embodiments may be practiced without these specific details. For example, well-known circuits, processes, algorithms, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Also, some embodiments are described as processes depicted as flow diagrams or block diagrams. Although each may describe the operations as a sequential process, many of the operations can be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention.

What is claimed is:

1. A computer implemented method, comprising:
creating a preventative care and health intervention computer application comprising modules to evaluate a health of a member based on healthcare provider defined weights to factors related to a health of the member and to gather data transmitted from an interconnected network of independent computing systems, including: (i) healthcare provider servers and devices, (ii) intervention program provider servers and devices, and (iii) patient-side servers and devices, wherein the independent computing systems communicate with each other to transmit and process a member's participation and attendance with mandated preventative health care and health intervention programs, wherein the mandated preventative health care and health intervention programs are configured to improve the health of the member, and wherein the mandated preventative health care and health intervention programs are categorized based on attributes related to health outcomes, effectiveness, and/or patient profiles and medical history,
wherein the mandated preventative health care and health intervention programs have measurable and trackable dimensions that are correlated to the modules of the preventative care and health intervention computer application, further comprising:
using a clinical decision module that is part of the preventative care and health intervention computer application and is configured to act as a data integration module, receiving and extracting an actual health status of the member further comprising assessing the actual health status of the member based on data related to a physical health, social health, and mental health of the member in order to establish a member's current health status, wherein the data is collected from the healthcare provider servers and devices storing clinical information and diagnostic information and medical records of the member as well as from third party devices and member provided information;
using a goal-setting module, collecting inputs from healthcare providers via a graphical interface of the preventative care and health intervention computer application for healthcare providers associated with the member to assign dimension-level custom weightings to determine health priorities that include physical, mental, and social dimensions;

receiving assigned dimension-level custom weightings or values from the healthcare providers and extracting and storing the assigned dimension-level custom weightings or values from the healthcare providers in the preventative care and health intervention computer application for the member;

calculating dimension-level health scores for physical, mental, and social dimensions by applying the healthcare provider defined weights that establish goals set by the healthcare providers for program level adherence and performance scores obtained from intervention program provider servers and devices and patient-side servers and devices storing data related to a member's attendance and adherence and participation level to the mandated preventative health care and health intervention programs to the member, wherein the mandated preventative health care and health intervention programs are categorized and assigned based on health outcomes, effectiveness, and/or patient profiles;

transmitting mandated preventative health care and health intervention programs to the intervention program provider servers and devices, and the patient-side servers and devices, to ensure real-time alignment of health intervention goals across the independent computing systems, wherein the mandated preventative health care and health intervention programs to the member are monitored and data is provided related to a member's performance and attendance and participation in the mandated preventative health care and health intervention programs;

using a progress tracking module, tracking the member's performance and attendance and participation in the mandated preventative health care and health intervention programs for a period of time, further comprising, assembling and compiling receivable data from a variety of sources, further comprising:
 tracking member self-reported data from patient-side servers and devices;
 reviewing data collected through third party sensors and wearable electronic devices; and
 automatically collecting evaluation and feedback from intervention program provider servers and devices of the one or more preventative health care and health intervention programs, further comprising, real-time adjustment of an initial score assessed for the member for the overall health score,
 wherein the receivable data is usable to assemble attendance data and performance data of the member for the one or more preventative health care and health intervention programs;

triggering a comparison between data related to member's attendance and adherence and participation level in the mandated preventative health care and health intervention program and the dimension-level health scores based on the healthcare provider defined weights further comprising:
 returning metrics for poor adherence or performance that are below a minimum threshold;
 returning metrics for acceptable adherence and performance that are at or above the minimum threshold;
 recalculating the initial score for the overall health score and generating an updated score while further accounting for the healthcare provider defined weights to physical dimensions, the social dimensions, and the mental dimensions;

using a recommendation module that integrates reporting and sharing, providing the updated score for the overall health score of the member with an updated recommendations for which mandated preventative health care and health intervention programs to attend based on the metrics returned and the updated score;

transmitting the updated recommendations to the intervention program provider servers and devices, and patient-side servers and devices, wherein the clinical decision module, the progress tracking module, and the recommendation module are interdependent and interact dynamically come together.

2. The computer implemented method of claim 1, further comprising collecting program information regarding program type data, program specification data, target member group data, health effect data from the intervention program provider servers and devices and patient-side servers and devices.

3. The computer implemented method of claim 2, further comprising aggregating program information, attendance, auto-detected performance, and trainer feedback data using the preventative care and health intervention computer application.

4. The computer implemented method of claim 1, wherein the initial score for the overall health of the member is based in part on an evaluation of genetic tests, lab tests and imaging data, prescription drug data, medical condition data, health counseling data, medical history data, demographic data, and organ system function data.

5. The computer implemented method of claim 1, wherein the initial physical, mental, and social health score for the overall health of the member comprises evaluating a financial status, occupation, living environment, social connectedness of the member.

6. The computer implemented method of claim 1, further comprising unlocking access to additional health intervention programs or health care programs to assist the member in improving the overall health score.

7. The computer implemented method of claim 1, further comprising rewarding the member with incentives provided through the preventative care and health intervention computer application if the overall physical, mental, and social health score is determined to improve on a scoring scale.

8. The computer implemented method of claim 7, wherein the incentives comprise monetary compensation, crypto currencies.

9. The computer implemented method of claim 7, wherein the incentives comprise redeemable points that can be used for travel, merchandise, gift cards, services, events, or donations.

10. The computer implemented method of claim 1, wherein the healthcare providers can assign extra weight to a select program of the selected programs in order to prioritize the select program in the overall physical, mental, and social health score.

* * * * *